US008277501B2

(12) United States Patent
Chalekian et al.

(10) Patent No.: US 8,277,501 B2
(45) Date of Patent: Oct. 2, 2012

(54) BI-STABLE BIFURCATED STENT PETAL GEOMETRY

(75) Inventors: Aaron Chalekian, Minneapolis, MN (US); Na Zhang, Maple Grove, MN (US); Michael P. Meyer, Richfield, MN (US); Tim Rossman, Hanover, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 509 days.

(21) Appl. No.: 11/962,456

(22) Filed: Dec. 21, 2007

(65) Prior Publication Data
US 2009/0163993 A1    Jun. 25, 2009

(51) Int. Cl.
*A61F 2/82*    (2006.01)
(52) U.S. Cl. ..................... 623/1.35; 623/1.15
(58) Field of Classification Search ........ 623/1.15–1.17, 623/1.2, 1.35; 606/191, 192, 194, 198
See application file for complete search history.

(56) References Cited

U.S. PATENT DOCUMENTS

| | | | |
|---|---|---|---|
| 4,309,994 A | 1/1982 | Grunwald |
| 4,769,005 A | 9/1988 | Ginsburg et al. |
| 4,774,949 A | 10/1988 | Fogarty |
| 4,896,670 A | 1/1990 | Crittenden |
| 4,905,667 A | 3/1990 | Foerster et al. |
| 4,906,244 A | 3/1990 | Pinchuk et al. |
| 4,935,190 A | 6/1990 | Tennerstedt |
| 4,994,071 A | 2/1991 | MacGregor |
| 5,037,392 A | 8/1991 | Hillstead |
| 5,053,007 A | 10/1991 | Euteneuer |
| 5,087,246 A | 2/1992 | Smith |
| 5,112,900 A | 5/1992 | Buddenhagen et al. |
| 5,147,302 A | 9/1992 | Euteneuer et al. |
| 5,163,989 A | 11/1992 | Campbell et al. |
| 5,209,799 A | 5/1993 | Vigil |
| 5,226,887 A | 7/1993 | Farr et al. |
| 5,306,246 A | 4/1994 | Sahatjian et al. |
| 5,318,587 A | 6/1994 | Davey |
| 5,342,307 A | 8/1994 | Euteneuer et al. |
| 5,342,387 A | 8/1994 | Summers |
| 5,348,538 A | 9/1994 | Wang et al. |
| 5,350,361 A | 9/1994 | Tsukashima et al. |
| 5,358,475 A | 10/1994 | Mares et al. |

(Continued)

FOREIGN PATENT DOCUMENTS

CA    2220864    7/1999

(Continued)

OTHER PUBLICATIONS

Hackworth et al., Development and First Application of Bistable Expandable Sand Screen, Society of Petroleum Engineers Inc., Copyright 2003.

(Continued)

*Primary Examiner* — Thomas J Sweet
*Assistant Examiner* — Yashita Sharma
(74) *Attorney, Agent, or Firm* — Vidas, Arrett and Steinkraus

(57) ABSTRACT

A stent has a substantially cylindrical tubular body with at least one expandable side branch that has a plurality of members. The plurality of members includes at least one first member having a first width and at least one second member having a second width, where the first width is greater than the second width. Each of the at least one first members and each of the at least one second members define a cell that has at least two stable cell geometries.

16 Claims, 21 Drawing Sheets

U.S. PATENT DOCUMENTS

| | | |
|---|---|---|
| 5,387,235 A | 2/1995 | Chuter |
| 5,403,340 A | 4/1995 | Wang et al. |
| 5,447,497 A | 9/1995 | Sogard et al. |
| 5,456,666 A | 10/1995 | Campbell et al. |
| 5,456,712 A | 10/1995 | Maginot |
| 5,458,572 A | 10/1995 | Campbell et al. |
| 5,476,471 A | 12/1995 | Shifrin et al. |
| 5,478,319 A | 12/1995 | Campbell et al. |
| 5,487,730 A | 1/1996 | Marcadis et al. |
| 5,523,092 A | 6/1996 | Hanson et al. |
| 5,549,552 A | 8/1996 | Peters et al. |
| 5,550,180 A | 8/1996 | Elsik et al. |
| 5,556,383 A | 9/1996 | Wang et al. |
| 5,591,228 A | 1/1997 | Edoga |
| 5,607,444 A | 3/1997 | Lam |
| 5,609,605 A | 3/1997 | Marshall et al. |
| 5,609,627 A | 3/1997 | Goicoechea et al. |
| 5,613,980 A | 3/1997 | Chauhan |
| 5,617,878 A | 4/1997 | Taheri |
| 5,632,762 A | 5/1997 | Myler |
| 5,632,763 A | 5/1997 | Glastra |
| 5,632,772 A | 5/1997 | Alcime et al. |
| 5,636,641 A | 6/1997 | Fariabi |
| 5,669,924 A | 9/1997 | Shaknovich |
| 5,669,932 A | 9/1997 | Fischell et al. |
| 5,676,697 A | 10/1997 | McDonald |
| 5,683,450 A | 11/1997 | Goicoechea et al. |
| 5,697,971 A | 12/1997 | Fischell et al. |
| 5,707,348 A | 1/1998 | Krogh |
| 5,709,713 A | 1/1998 | Evans et al. |
| 5,718,684 A | 2/1998 | Gupta |
| 5,718,724 A | 2/1998 | Goicoechea et al. |
| 5,720,735 A | 2/1998 | Dorros |
| 5,746,745 A | 5/1998 | Abele et al. |
| 5,749,825 A | 5/1998 | Fischell et al. |
| 5,749,890 A | 5/1998 | Shaknovich |
| 5,755,734 A | 5/1998 | Richter et al. |
| 5,755,735 A | 5/1998 | Richter et al. |
| 5,755,771 A | 5/1998 | Penn et al. |
| 5,755,773 A | 5/1998 | Evans et al. |
| 5,755,778 A | 5/1998 | Kleshinski |
| 5,782,906 A | 7/1998 | Marshall et al. |
| 5,800,520 A | 9/1998 | Fogarty et al. |
| 5,810,767 A | 9/1998 | Klein |
| 5,824,036 A | 10/1998 | Lauterjung |
| 5,824,040 A | 10/1998 | Cox et al. |
| 5,827,320 A | 10/1998 | Richter et al. |
| 5,830,182 A | 11/1998 | Wang et al. |
| 5,833,657 A | 11/1998 | Reinhardt et al. |
| 5,843,172 A | 12/1998 | Yan |
| 5,851,464 A | 12/1998 | Davila et al. |
| 5,868,777 A | 2/1999 | Lam |
| 5,882,334 A | 3/1999 | Sepetka et al. |
| 5,891,108 A | 4/1999 | Leone et al. |
| 5,893,887 A | 4/1999 | Jayaraman |
| 5,906,640 A | 5/1999 | Penn et al. |
| 5,922,020 A | 7/1999 | Klein et al. |
| 5,922,021 A | 7/1999 | Jang |
| 5,951,941 A | 9/1999 | Wang et al. |
| 5,961,548 A | 10/1999 | Shmulewitz |
| 5,972,017 A | 10/1999 | Berg et al. |
| 5,972,027 A | 10/1999 | Johnson |
| 6,013,054 A | 1/2000 | Jiun Yan |
| 6,013,055 A | 1/2000 | Bampos et al. |
| 6,013,091 A | 1/2000 | Ley et al. |
| 6,017,324 A | 1/2000 | Tu et al. |
| 6,017,363 A | 1/2000 | Hojeibane |
| 6,030,414 A | 2/2000 | Taheri |
| 6,033,380 A | 3/2000 | Butaric et al. |
| 6,033,433 A | 3/2000 | Ehr et al. |
| 6,033,434 A | 3/2000 | Borghi |
| 6,033,435 A | 3/2000 | Penn et al. |
| 6,048,361 A | 4/2000 | Von Oepen |
| 6,056,775 A | 5/2000 | Borghi et al. |
| 6,059,824 A | 5/2000 | Taheri |
| 6,068,655 A | 5/2000 | Seguin et al. |
| 6,071,285 A | 6/2000 | Lashinski et al. |
| 6,071,305 A | 6/2000 | Brown et al. |
| 6,086,611 A | 7/2000 | Duffy et al. |
| 6,093,203 A | 7/2000 | Uflacker |
| 6,096,070 A | 8/2000 | Ragheb et al. |
| 6,096,073 A | 8/2000 | Webster et al. |
| 6,099,497 A | 8/2000 | Adams et al. |
| 6,113,579 A | 9/2000 | Eidenschink et al. |
| 6,117,117 A | 9/2000 | Mauch |
| 6,117,156 A | 9/2000 | Richter et al. |
| 6,123,721 A | 9/2000 | Jang |
| 6,126,652 A | 10/2000 | McLeod et al. |
| 6,129,738 A | 10/2000 | Lashinski et al. |
| 6,129,754 A | 10/2000 | Kanesaka et al. |
| 6,135,982 A | 10/2000 | Campbell |
| 6,142,973 A | 11/2000 | Carleton et al. |
| 6,143,002 A | 11/2000 | Vietmeier |
| 6,146,356 A | 11/2000 | Wang et al. |
| 6,159,238 A | 12/2000 | Killion et al. |
| 6,165,195 A | 12/2000 | Wilson et al. |
| 6,168,621 B1 | 1/2001 | Vrba |
| 6,171,278 B1 | 1/2001 | Wang et al. |
| 6,183,509 B1 | 2/2001 | Dibie |
| 6,190,404 B1 | 2/2001 | Palmaz et al. |
| 6,203,568 B1 | 3/2001 | Lombardi et al. |
| 6,206,915 B1 | 3/2001 | Fagan et al. |
| 6,206,916 B1 | 3/2001 | Furst |
| 6,210,380 B1 | 4/2001 | Mauch |
| 6,210,429 B1 | 4/2001 | Vardi et al. |
| 6,210,433 B1 | 4/2001 | Larre |
| 6,210,436 B1 | 4/2001 | Weadock |
| 6,231,598 B1 | 5/2001 | Berry et al. |
| 6,240,616 B1 | 6/2001 | Yan |
| 6,241,762 B1 | 6/2001 | Shanley |
| 6,253,443 B1 | 7/2001 | Johnson |
| 6,254,593 B1 | 7/2001 | Wilson |
| 6,254,632 B1 | 7/2001 | Wu et al. |
| 6,258,115 B1 | 7/2001 | Dubrul |
| 6,258,116 B1 | 7/2001 | Hojeibane |
| 6,258,121 B1 | 7/2001 | Yang et al. |
| 6,261,305 B1 | 7/2001 | Marotta et al. |
| 6,261,316 B1 | 7/2001 | Shaolian et al. |
| 6,261,320 B1 | 7/2001 | Tam et al. |
| 6,264,662 B1 | 7/2001 | Lauterjung |
| 6,264,686 B1 | 7/2001 | Rieu et al. |
| 6,273,908 B1 | 8/2001 | Ndonda-Lay |
| 6,273,913 B1 | 8/2001 | Wright et al. |
| 6,280,413 B1 | 8/2001 | Clark et al. |
| 6,287,628 B1 | 9/2001 | Hossainy et al. |
| 6,290,673 B1 | 9/2001 | Shanley |
| 6,293,967 B1 | 9/2001 | Shanley |
| 6,293,968 B1 | 9/2001 | Taheri |
| 6,325,826 B1 | 12/2001 | Vardi et al. |
| 6,328,925 B1 | 12/2001 | Wang et al. |
| 6,334,864 B1 | 1/2002 | Amplatz et al. |
| 6,334,870 B1 | 1/2002 | Ehr et al. |
| 6,346,089 B1 | 2/2002 | Dibie |
| 6,348,065 B1 | 2/2002 | Brown et al. |
| 6,355,060 B1 | 3/2002 | Lenker et al. |
| 6,358,552 B1 | 3/2002 | Mandralis et al. |
| 6,361,544 B1 | 3/2002 | Wilson et al. |
| 6,361,555 B1 | 3/2002 | Wilson |
| 6,379,381 B1 | 4/2002 | Hossainy et al. |
| 6,383,213 B2 | 5/2002 | Wilson et al. |
| 6,395,018 B1 | 5/2002 | Castaneda |
| 6,395,326 B1 | 5/2002 | Castro et al. |
| 6,406,457 B1 | 6/2002 | Wang et al. |
| 6,423,091 B1 | 7/2002 | Hojeibane |
| 6,436,104 B2 | 8/2002 | Hojeibane |
| 6,436,134 B2 | 8/2002 | Richter et al. |
| 6,478,816 B1 | 11/2002 | Kveen et al. |
| 6,488,702 B1 | 12/2002 | Besselink |
| 6,491,666 B1 | 12/2002 | Santini, Jr. et al. |
| 6,506,437 B1 | 1/2003 | Harish et al. |
| 6,508,836 B2 | 1/2003 | Wilson et al. |
| 6,517,558 B2 | 2/2003 | Gittings et al. |
| 6,520,988 B1 | 2/2003 | Colombo et al. |
| 6,527,762 B1 | 3/2003 | Santini, Jr. et al. |
| 6,527,799 B2 | 3/2003 | Shanley |
| 6,537,256 B2 | 3/2003 | Santini, Jr. et al. |
| 6,540,779 B2 | 4/2003 | Richter et al. |

| | | | | | | |
|---|---|---|---|---|---|---|
| 6,551,351 B2 | 4/2003 | Smith et al. | | 2002/0026232 A1 | 2/2002 | Marotta et al. |
| 6,551,838 B2 | 4/2003 | Santini, Jr. et al. | | 2002/0035392 A1 | 3/2002 | Wilson |
| 6,558,422 B1 | 5/2003 | Baker et al. | | 2002/0038146 A1 | 3/2002 | Harry |
| 6,562,065 B1 | 5/2003 | Shanley | | 2002/0042650 A1 | 4/2002 | Vardi et al. |
| 6,579,309 B1 | 6/2003 | Loos et al. | | 2002/0052648 A1 | 5/2002 | McGuckin, Jr. et al. |
| 6,579,312 B2 | 6/2003 | Wilson et al. | | 2002/0072790 A1 | 6/2002 | McGuckin, Jr. et al. |
| 6,582,394 B1 | 6/2003 | Reiss et al. | | 2002/0095208 A1 | 7/2002 | Gregorich et al. |
| 6,596,020 B2 | 7/2003 | Vardi et al. | | 2002/0107562 A1 | 8/2002 | Hart |
| 6,599,316 B2 | 7/2003 | Vardi et al. | | 2002/0111675 A1 | 8/2002 | Wilson |
| 6,638,302 B1 | 10/2003 | Curcio et al. | | 2002/0156516 A1 | 10/2002 | Vardi et al. |
| 6,645,242 B1 | 11/2003 | Quinn | | 2002/0156517 A1 | 10/2002 | Perouse |
| 6,656,162 B2 | 12/2003 | Santini, Jr. et al. | | 2002/0163104 A1 | 11/2002 | Motsenbocker et al. |
| 6,669,683 B2 | 12/2003 | Santini, Jr. et al. | | 2002/0165604 A1 | 11/2002 | Shanley |
| 6,689,156 B1 | 2/2004 | Davidson et al. | | 2002/0173835 A1 | 11/2002 | Bourang et al. |
| 6,692,483 B2 | 2/2004 | Vardi et al. | | 2002/0173840 A1 | 11/2002 | Brucker et al. |
| 6,695,877 B2 | 2/2004 | Brucker et al. | | 2002/0183763 A1 | 12/2002 | Callol et al. |
| 6,706,062 B2 | 3/2004 | Vardi et al. | | 2002/0193872 A1 | 12/2002 | Trout, III et al. |
| 6,709,379 B1 | 3/2004 | Brandau et al. | | 2002/0193873 A1 | 12/2002 | Brucker et al. |
| 6,713,119 B2 | 3/2004 | Hossainy et al. | | 2003/0009209 A1 | 1/2003 | Hojeibane |
| 6,730,064 B2 | 5/2004 | Ragheb et al. | | 2003/0028233 A1 | 2/2003 | Vardi et al. |
| 6,749,628 B1 | 6/2004 | Callol et al. | | 2003/0050688 A1 | 3/2003 | Fischell et al. |
| 6,758,859 B1 | 7/2004 | Dang et al. | | 2003/0055378 A1 | 3/2003 | Wang et al. |
| 6,764,507 B2 | 7/2004 | Shanley et al. | | 2003/0055483 A1 | 3/2003 | Gumm |
| 6,773,429 B2 | 8/2004 | Sheppard, Jr. et al. | | 2003/0074047 A1 | 4/2003 | Richter |
| 6,776,793 B2 | 8/2004 | Brown et al. | | 2003/0083687 A1 | 5/2003 | Pallazza |
| 6,783,543 B2 | 8/2004 | Jang | | 2003/0093109 A1 | 5/2003 | Mauch |
| 6,790,228 B2 | 9/2004 | Hossainy et al. | | 2003/0097169 A1 | 5/2003 | Brucker |
| 6,811,566 B1 | 11/2004 | Penn et al. | | 2003/0105511 A1 | 6/2003 | Welsh et al. |
| 6,827,250 B2 | 12/2004 | Uhland et al. | | 2003/0114912 A1 | 6/2003 | Sequin et al. |
| 6,835,203 B1 | 12/2004 | Vardi et al. | | 2003/0125791 A1 | 7/2003 | Sequin et al. |
| 6,858,038 B2 | 2/2005 | Heuser | | 2003/0125802 A1 | 7/2003 | Callol et al. |
| 6,884,258 B2 | 4/2005 | Vardi et al. | | 2003/0135259 A1 | 7/2003 | Simso |
| 6,896,699 B2 | 5/2005 | Wilson et al. | | 2003/0163157 A1 | 8/2003 | McMorrow et al. |
| 6,904,658 B2 | 6/2005 | Hines | | 2003/0167085 A1 | 9/2003 | Shanley |
| 6,932,837 B2 | 8/2005 | Amplatz et al. | | 2003/0181923 A1 | 9/2003 | Vardi |
| 6,946,092 B1 | 9/2005 | Bertolino et al. | | 2003/0195606 A1 | 10/2003 | Davidson et al. |
| 6,955,687 B2 | 10/2005 | Richter et al. | | 2003/0199970 A1 | 10/2003 | Shanley |
| 6,955,688 B2 | 10/2005 | Wilson et al. | | 2004/0006381 A1 | 1/2004 | Sequin et al. |
| 6,962,602 B2 | 11/2005 | Vardi et al. | | 2004/0015227 A1 | 1/2004 | Vardi et al. |
| 6,989,071 B2 | 1/2006 | Kocur et al. | | 2004/0044396 A1 | 3/2004 | Clerc et al. |
| 7,018,400 B2 | 3/2006 | Lashinski et al. | | 2004/0059406 A1 | 3/2004 | Cully et al. |
| 7,022,131 B1 | 4/2006 | Derowe et al. | | 2004/0068161 A1 | 4/2004 | Couvillon, Jr. |
| 7,041,130 B2 | 5/2006 | Santini, Jr. et al. | | 2004/0073294 A1 | 4/2004 | Diaz et al. |
| 7,052,488 B2 | 5/2006 | Uhland | | 2004/0088007 A1 | 5/2004 | Eidenschink |
| 7,056,323 B2 | 6/2006 | Mareiro et al. | | 2004/0093071 A1 | 5/2004 | Jang |
| 7,056,338 B2 | 6/2006 | Shanley et al. | | 2004/0117003 A1 | 6/2004 | Ouriel et al. |
| 7,060,084 B1 | 6/2006 | Loshakove et al. | | 2004/0122505 A1 | 6/2004 | Shanley |
| 7,060,091 B2 | 6/2006 | Killion et al. | | 2004/0122506 A1 | 6/2004 | Shanley et al. |
| 7,070,616 B2 | 7/2006 | Majercak et al. | | 2004/0127976 A1 | 7/2004 | Diaz |
| 7,160,321 B2 | 1/2007 | Shanley et al. | | 2004/0127977 A1 | 7/2004 | Shanley |
| 7,169,175 B2 | 1/2007 | Cottone, Jr. et al. | | 2004/0133268 A1 | 7/2004 | Davidson et al. |
| 7,169,179 B2 | 1/2007 | Shanley et al. | | 2004/0138732 A1 | 7/2004 | Suhr et al. |
| 7,179,288 B2 | 2/2007 | Shanley | | 2004/0138737 A1 | 7/2004 | Davidson et al. |
| 7,179,289 B2 | 2/2007 | Shanley | | 2004/0142014 A1 | 7/2004 | Litvack et al. |
| 7,208,010 B2 | 4/2007 | Shanley et al. | | 2004/0143321 A1 | 7/2004 | Litvack et al. |
| 7,208,011 B2 | 4/2007 | Shanley et al. | | 2004/0143322 A1 | 7/2004 | Litvack et al. |
| 7,220,275 B2 | 5/2007 | Davidson et al. | | 2004/0148006 A1 | 7/2004 | Davidson et al. |
| 7,235,097 B2 | 6/2007 | Calisse et al. | | 2004/0148012 A9 | 7/2004 | Jang |
| 7,722,658 B2 * | 5/2010 | Richter et al. ............... 623/1.15 | | 2004/0172121 A1 | 9/2004 | Eidenschink et al. |
| 7,959,668 B2 * | 6/2011 | Yadin ......................... 623/1.35 | | 2004/0186560 A1 | 9/2004 | Alt |
| 2001/0003161 A1 | 6/2001 | Vardi et al. | | 2004/0202692 A1 | 10/2004 | Shanley et al. |
| 2001/0004706 A1 | 6/2001 | Hojeibane | | 2004/0204750 A1 | 10/2004 | Dinh |
| 2001/0004707 A1 | 6/2001 | Dereume et al. | | 2004/0215227 A1 | 10/2004 | McMorrow et al. |
| 2001/0012927 A1 | 8/2001 | Mauch | | 2004/0220661 A1 | 11/2004 | Shanley et al. |
| 2001/0016766 A1 | 8/2001 | Vardi et al. | | 2004/0225345 A1 | 11/2004 | Fischell et al. |
| 2001/0016767 A1 | 8/2001 | Wilson et al. | | 2004/0236408 A1 | 11/2004 | Shanley |
| 2001/0016768 A1 | 8/2001 | Wilson et al. | | 2004/0249449 A1 | 12/2004 | Shanley et al. |
| 2001/0025195 A1 | 9/2001 | Shaolian et al. | | 2004/0267352 A1 | 12/2004 | Davidson et al. |
| 2001/0027291 A1 | 10/2001 | Shanley | | 2005/0004656 A1 | 1/2005 | Das |
| 2001/0027338 A1 | 10/2001 | Greenberg | | 2005/0010278 A1 | 1/2005 | Vardi et al. |
| 2001/0029396 A1 | 10/2001 | Wilson et al. | | 2005/0015108 A1 | 1/2005 | Williams et al. |
| 2001/0037116 A1 | 11/2001 | Wilson et al. | | 2005/0015135 A1 | 1/2005 | Shanley |
| 2001/0037138 A1 | 11/2001 | Wilson et al. | | 2005/0043816 A1 | 2/2005 | Datta et al. |
| 2001/0039448 A1 | 11/2001 | Dibie | | 2005/0060027 A1 | 3/2005 | Khenansho et al. |
| 2001/0049552 A1 | 12/2001 | Richter et al. | | 2005/0096726 A1 | 5/2005 | Sequin et al. |
| 2001/0056297 A1 | 12/2001 | Hojeibane | | 2005/0102017 A1 | 5/2005 | Mattison |
| 2002/0013618 A1 | 1/2002 | Marotta et al. | | 2005/0102021 A1 | 5/2005 | Osborne |
| 2002/0013619 A1 | 1/2002 | Shanley | | 2005/0102023 A1 | 5/2005 | Yadin et al. |
| 2002/0022874 A1 | 2/2002 | Wilson | | 2005/0119731 A1 | 6/2005 | Brucker et al. |

| | | | | | | |
|---|---|---|---|---|---|---|
| 2005/0125076 A1 | 6/2005 | Ginn | | WO | 97/07752 | 3/1997 |
| 2005/0131526 A1 | 6/2005 | Wong | | WO | 97/15346 | 5/1997 |
| 2005/0149161 A1 | 7/2005 | Eidenschink et al. | | WO | 97/16217 | 5/1997 |
| 2005/0154442 A1 | 7/2005 | Eidenschink et al. | | WO | 97/26936 | 7/1997 |
| 2005/0154444 A1 | 7/2005 | Quadri | | WO | 97/41803 | 11/1997 |
| 2005/0183259 A1 | 8/2005 | Eidenschink et al. | | WO | 97/45073 | 12/1997 |
| 2005/0187602 A1 | 8/2005 | Eidenschink | | WO | 97/46174 | 12/1997 |
| 2005/0187611 A1 | 8/2005 | Ding et al. | | WO | 98/19628 | 5/1998 |
| 2005/0192657 A1 | 9/2005 | Colen et al. | | WO | 98/23228 | 6/1998 |
| 2005/0209673 A1 | 9/2005 | Shaked | | WO | 9832412 | 7/1998 |
| 2005/0222668 A1 | 10/2005 | Schaeffer et al. | | WO | 98/36709 | 8/1998 |
| 2005/0228483 A1 | 10/2005 | Kaplan et al. | | WO | 98/36784 | 8/1998 |
| 2005/0273149 A1 | 12/2005 | Tran et al. | | WO | 98/37833 | 9/1998 |
| 2006/0015134 A1 | 1/2006 | Trinidad | | WO | 98/47447 | 10/1998 |
| 2006/0034884 A1 | 2/2006 | Stenzel | | WO | 98/48879 | 11/1998 |
| 2006/0036315 A1 | 2/2006 | Yadin et al. | | WO | 99/03426 | 1/1999 |
| 2006/0041303 A1 | 2/2006 | Israel | | WO | 99/04726 | 2/1999 |
| 2006/0045901 A1 | 3/2006 | Weber | | WO | 99/15103 | 4/1999 |
| 2006/0079956 A1 | 4/2006 | Eigler et al. | | WO | 99/15108 | 4/1999 |
| 2006/0088654 A1 | 4/2006 | Ding et al. | | WO | 99/15109 | 4/1999 |
| 2006/0093643 A1 | 5/2006 | Stenzel | | WO | 99/23977 | 5/1999 |
| 2006/0100686 A1 | 5/2006 | Bolduc | | WO | 99/24104 | 5/1999 |
| 2006/0122698 A1 | 6/2006 | Spencer et al. | | WO | 99/29262 | 6/1999 |
| 2006/0155360 A1 | 7/2006 | Calisse et al. | | WO | 99/34749 | 7/1999 |
| 2006/0173528 A1 | 8/2006 | Feld et al. | | WO | 99/36002 | 7/1999 |
| 2006/0206188 A1 | 9/2006 | Weber et al. | | WO | 99/36015 | 7/1999 |
| 2006/0217795 A1 | 9/2006 | Besselink et al. | | WO | 99/44539 | 9/1999 |
| 2006/0287712 A1 | 12/2006 | Eidenschink | | WO | 99/56661 | 11/1999 |
| 2007/0005126 A1 | 1/2007 | Tischler | | WO | 99/65419 | 12/1999 |
| 2007/0050016 A1 | 3/2007 | Gregorich et al. | | WO | 00/07523 | 2/2000 |
| 2007/0073376 A1 | 3/2007 | Krolik et al. | | WO | 00/10489 | 3/2000 |
| 2007/0073384 A1 | 3/2007 | Brown et al. | | WO | 00/16719 | 3/2000 |
| 2007/0100434 A1 | 5/2007 | Gregorich et al. | | WO | 00/27307 | 5/2000 |
| 2007/0135904 A1 | 6/2007 | Eidenschink et al. | | WO | 00/27463 | 5/2000 |
| 2007/0173787 A1 | 7/2007 | Huang et al. | | WO | 00/28922 | 5/2000 |
| 2007/0173923 A1 | 7/2007 | Savage et al. | | WO | 01/45594 | 6/2000 |
| 2007/0208408 A1 | 9/2007 | Weber et al. | | WO | 00/44307 | 8/2000 |
| | | | | WO | 00/44309 | 8/2000 |
| FOREIGN PATENT DOCUMENTS | | | | WO | 00/47134 | 8/2000 |
| DE | 9014845 | 2/1991 | | WO | 00/48531 | 8/2000 |
| DE | 29701758 | 3/1997 | | WO | 00/49951 | 8/2000 |
| DE | 29701883 | 5/1997 | | WO | 00/51523 | 9/2000 |
| DE | 19921788 | 11/2000 | | WO | 00/57813 | 10/2000 |
| EP | 0479730 | 10/1991 | | WO | 00/67673 | 11/2000 |
| EP | 0565796 | 10/1993 | | WO | 00/71054 | 11/2000 |
| EP | 0751752 | 1/1997 | | WO | 00/71055 | 11/2000 |
| EP | 0783873 | 7/1997 | | WO | 00/74595 | 12/2000 |
| EP | 0804907 | 11/1997 | | WO | 01/17577 | 3/2001 |
| EP | 0479557 | 7/1998 | | WO | 01/21095 | 3/2001 |
| EP | 0876805 | 11/1998 | | WO | 01/21109 | 3/2001 |
| EP | 0880949 | 12/1998 | | WO | 01/21244 | 3/2001 |
| EP | 0891751 | 1/1999 | | WO | 01/26584 | 4/2001 |
| EP | 0895759 | 2/1999 | | WO | 01/35715 | 5/2001 |
| EP | 0904745 | 3/1999 | | WO | 01/35863 | 5/2001 |
| EP | 0937442 | 8/1999 | | WO | 01/39697 | 6/2001 |
| EP | 0950386 | 10/1999 | | WO | 01/39699 | 6/2001 |
| EP | 0347023 | 12/1999 | | WO | 01/41677 | 6/2001 |
| EP | 1031328 | 8/2000 | | WO | 01/43665 | 6/2001 |
| EP | 1031329 | 8/2000 | | WO | 01/43809 | 6/2001 |
| EP | 0883384 | 12/2000 | | WO | 01/45785 | 6/2001 |
| EP | 0862392 | 8/2001 | | WO | 01/49342 | 7/2001 |
| EP | 0808140 | 12/2001 | | WO | 01/54621 | 8/2001 |
| EP | 0884028 | 2/2002 | | WO | 01/54622 | 8/2001 |
| EP | 1190685 | 3/2002 | | WO | 01/58385 | 8/2001 |
| EP | 0897700 | 7/2002 | | WO | 01/60284 | 8/2001 |
| EP | 0684022 | 2/2004 | | WO | 01/66036 | 9/2001 |
| EP | 1157674 | 7/2005 | | WO | 01/70294 | 9/2001 |
| EP | 1031330 | 11/2005 | | WO | 01/70299 | 9/2001 |
| EP | 1070513 | 6/2006 | | WO | 01/74273 | 10/2001 |
| FR | 2678508 | 1/1993 | | WO | 01/91918 | 12/2001 |
| FR | 2740346 | 10/1995 | | WO | 01/93781 | 12/2001 |
| FR | 2756173 | 11/1996 | | WO | 02/00138 | 1/2002 |
| GB | 2337002 | 5/1998 | | WO | 02/053066 | 7/2002 |
| WO | 88/06026 | 8/1988 | | WO | 02/068012 | 9/2002 |
| WO | 94/23787 | 10/1994 | | WO | 03/007842 | 1/2003 |
| WO | 95/21592 | 8/1995 | | WO | 03/055414 | 7/2003 |
| WO | 96/29955 | 10/1996 | | WO | 03/063924 | 8/2003 |
| WO | 96/34580 | 11/1996 | | WO | 2004/026174 | 4/2004 |
| WO | 96/41592 | 12/1996 | | WO | 2004/026180 | 4/2004 |

| WO | 2005/009295 | 2/2005 |
| WO | 2005/014077 | 2/2005 |
| WO | 2005/041810 | 5/2005 |
| WO | 2005/122959 | 12/2005 |
| WO | 2006/028925 | 3/2006 |
| WO | 2006/074476 | 7/2006 |
| WO | 2006/127127 | 11/2006 |

OTHER PUBLICATIONS

U.S. Appl. No. 60/844011, filed Sep. 12, 2006; Inventor: Broome et al.

U.S. Appl. No. 09/663,111, filed Sep. 15, 2000; Inventor: Davidson et al.

U.S. Appl. No. 09/614,472, filed Jul. 11, 2000; Inventor: Davidson et al.

U.S. Appl. No. 09/325,996, filed Jun. 4, 1999; Inventor: Vardi et al.

Chevalier, M.D., Bernard, "Placement of Coronary Stents in Bifurcation Lesions by the "Culotte" Technique," The American Journal of Cardiology, vol. 82, pp. 943-949 (Oct. 15, 1998).

Nakamura M.D., Shigeru, "Techniques for Palmaz-Schatz Stent Deployment in Lesions with a Large Side Branch," Catheterization and Cardiovascular Diagnosis, vol. 34, pp. 353-361 (1995).

Caputo, Ronald P., "Stent Jail: A Minimum-Security Prison," The American Journal of Cardiology, vol. 77, pp. 1226-1230 (Jun. 1, 1996).

Colombo, M.D., Antonio, ""Kissing" Stent for Bifurcational Coronary Lesions," Catheterization and Cardiovascular Diagnosis, vol. 30, pp. 327-330 (Dec. 1993).

Carrie, M.D., Didier, ""T"-Shaped Stent Placement: A Technique for the Treatment of Dissected Bifurcation Lesions," Catheterization and Cardiovascular Diagnosis, vol. 37 pp. 311-313 (Mar. 1996).

Katoh, M.D., Osamu, "New Double Wire Technique to Stent Ostial Lesions," Catheterization and Cardiovascular Diagnosis, vol. 40, pp. 400-402 (Apr. 1997).

Lewis, M.D., Bruce E., "Acute procedural results in the treatment of 30 coronary artery bifurcation lesions with a double-wire atherectomy technique for side-branch protection," American Heart Journal, vol. 127:6, pp. 1600-1607 (Jun. 1994).

Yamashita, M.D., PhD., Takehiro, "Birfurcation Lesions: Two Stents Versus One Stent—Immediate and Follow-up Results," Journal of the American College of Cardiology, vol. 35:5, pp. 1145-1151 (Apr. 2000).

Satler, M.D., Lowell F., "Bifurcation Disease: To Treat or Not to Treat," Catheterization and Cardiovascular Interventions, vol. 50, pp. 411-412 (2000).

* cited by examiner

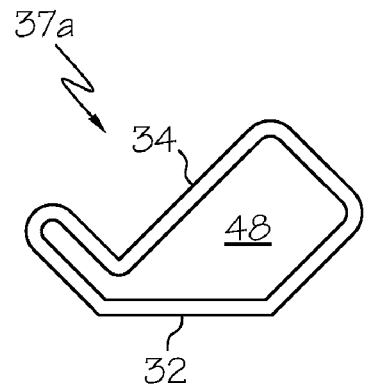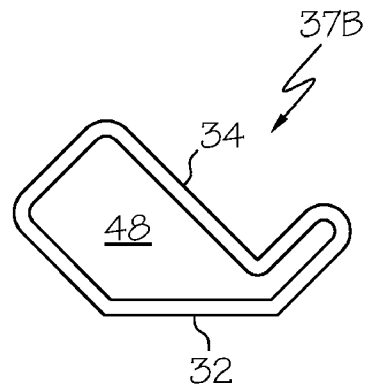
FIG. 8B    FIG. 8C
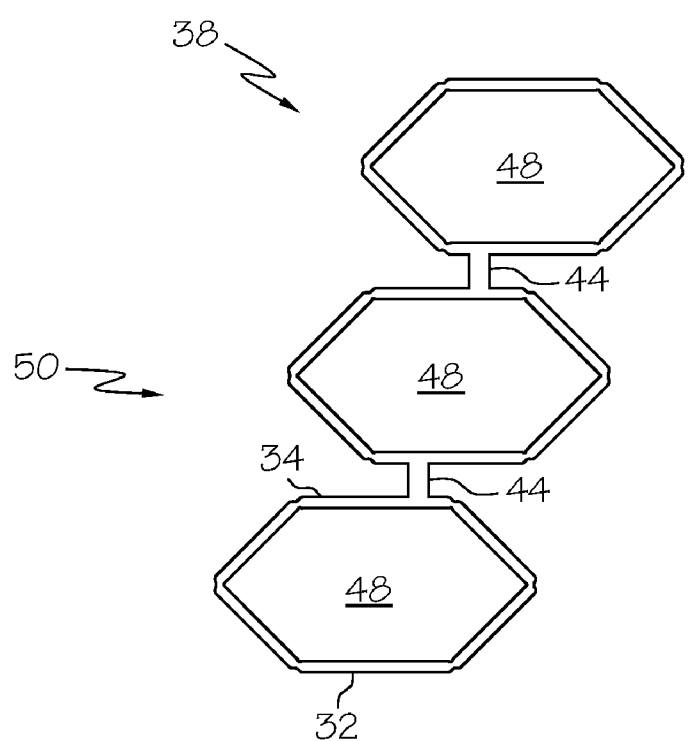
FIG. 8E

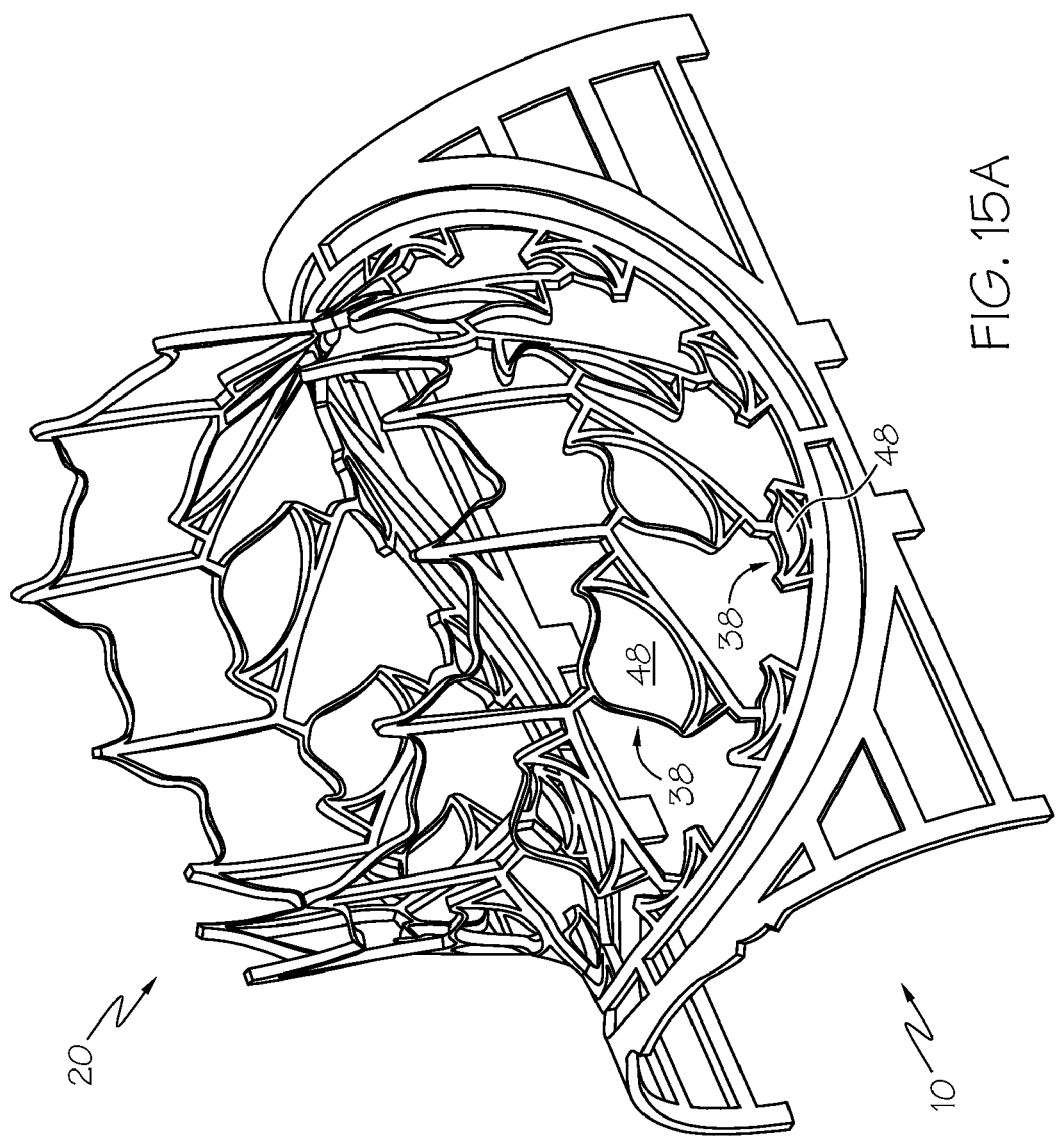

BI-STABLE BIFURCATED STENT PETAL GEOMETRY

CROSS-REFERENCE TO RELATED APPLICATIONS

Not Applicable

STATEMENT REGARDING FEDERALLY SPONSORED RESEARCH

Not Applicable

BACKGROUND OF THE INVENTION

A stent is a medical device introduced to a body lumen and is well known in the art. Typically, a stent is implanted in a blood vessel at the site of a stenosis or aneurysm endoluminally, i.e. by so-called "minimally invasive techniques" in which the stent in a radially reduced configuration, optionally restrained in a radially compressed configuration by a sheath and/or catheter, is delivered by a stent delivery system or "introducer" to the site where it is required. The introducer may enter the body from an access location outside the body, such as through the patient's skin, or by a "cut down" technique in which the entry blood vessel is exposed by minor surgical means.

Stents, grafts, stent-grafts, vena cava filters, expandable frameworks, and similar implantable medical devices are radially expandable endoprostheses which are typically intravascular implants capable of being implanted transluminally and enlarged radially after being introduced percutaneously. Stents may be implanted in a variety of body lumens or vessels such as within the vascular system, urinary tracts, bile ducts, fallopian tubes, coronary vessels, secondary vessels, etc. They may be self-expanding, expanded by an internal radial force, such as when mounted on a balloon, or a combination of self-expanding and balloon expandable (hybrid expandable).

Stents may be created by methods including cutting or etching a design from a tubular stock, from a flat sheet which is cut or etched and which is subsequently rolled or from one or more interwoven wires or braids.

Within the vasculature, it is not uncommon for stenoses to form at a vessel bifurcation. A bifurcation is an area of the vasculature or other portion of the body where a first (or parent) vessel is bifurcated into two or more branch vessels. Where a stenotic lesion or lesions form at such a bifurcation, the lesion(s) can affect only one of the vessels (i.e., either of the branch vessels or the parent vessel) two of the vessels, or all three vessels. Many prior art stents however are not wholly satisfactory for use where the site of desired application of the stent is juxtaposed or extends across a bifurcation in an artery or vein such, for example, as the bifurcation in the mammalian aortic artery into the common iliac arteries.

The art referred to and/or described above is not intended to constitute an admission that any patent, publication or other information referred to herein is "prior art" with respect to this invention. In addition, this section should not be construed to mean that a search has been made or that no other pertinent information as defined in 37 C.F.R. §1.56(a) exists.

All US patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

BRIEF SUMMARY OF THE INVENTION

In at least one embodiment, the invention is directed to a stent with a side branch comprising a plurality of members defining at least one cell having at least two stable cell geometries, a "bi-stable" cell. In some embodiments, some of the plurality of members of the stent form a double bi-stable cell geometry. In other embodiments, at least one of the members defining the bi-stable cell has at least one hinge. In some embodiments, the side branch has a plurality of cells having at least two stable cell geometries arranged in a column.

These and other embodiments which characterize the invention are pointed out with particularity in the claims annexed hereto and forming a part hereof. However, for further understanding of the invention, its advantages and objectives obtained by its use, reference can be made to the drawings which form a further part hereof and the accompanying descriptive matter, in which there is illustrated and described an embodiments of the invention.

BRIEF DESCRIPTION OF THE SEVERAL VIEWS OF THE DRAWING(S)

A detailed description of the invention is hereafter described with specific reference being made to the drawings.

FIG. 8B is one of the bi-stable cells in FIG. 8A in an intermediate state.

FIG. 8C is one of the bi-stable cells in FIG. 8A in an alternative intermediate state.

FIG. 8E is a view of a column of a plurality of cells in where adjacent cells are offset from one another.

Figure 12:
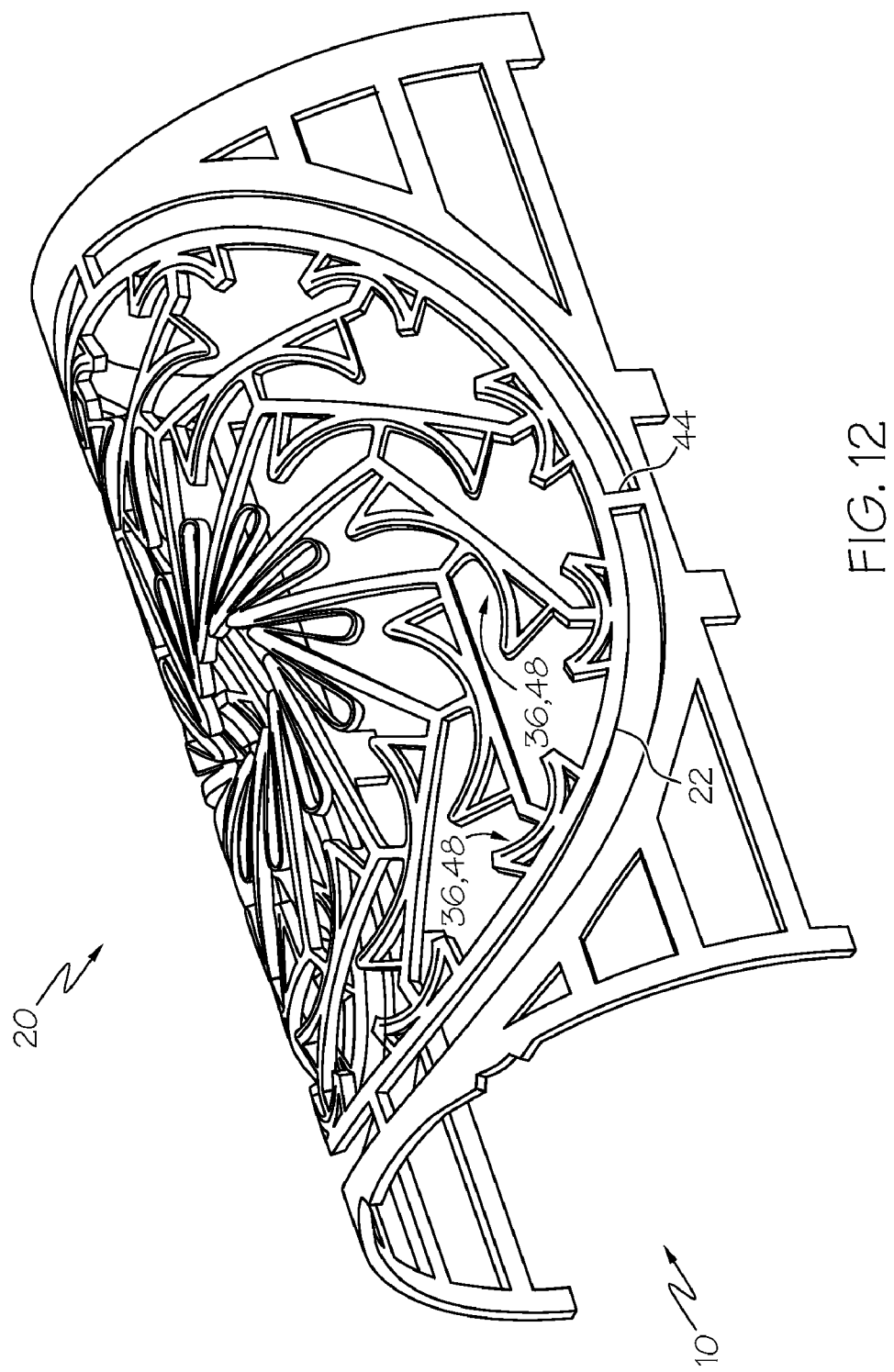
FIG. 12 is a perspective view of a portion of a stent with the side branch of FIG. 11A in an unexpanded state, and the bi-stable cells in a first state.
Figure 13:
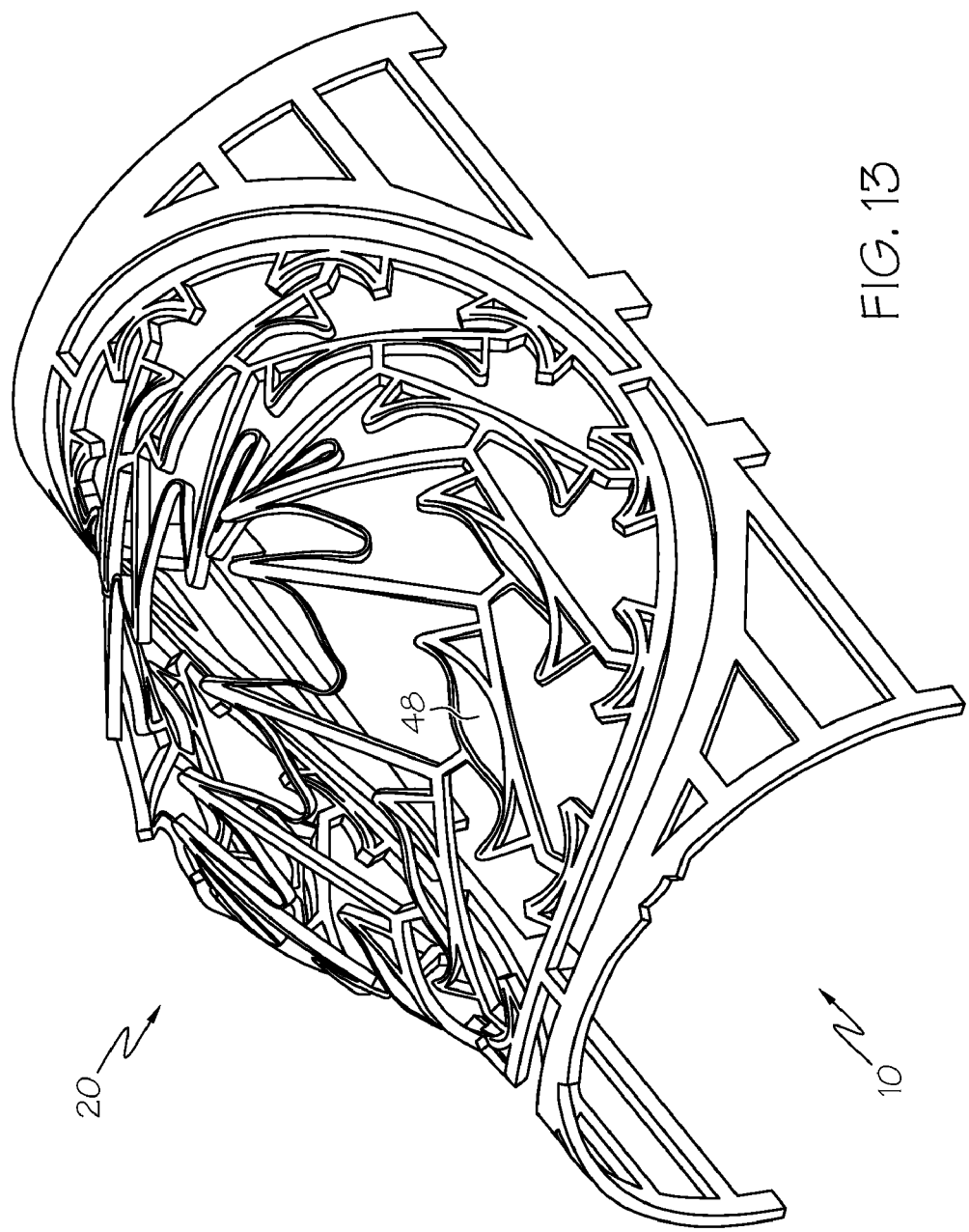

FIG. 13 a perspective view of the stent portion of FIG. 12 with the side branch in a partially expanded state.

Figure 14:
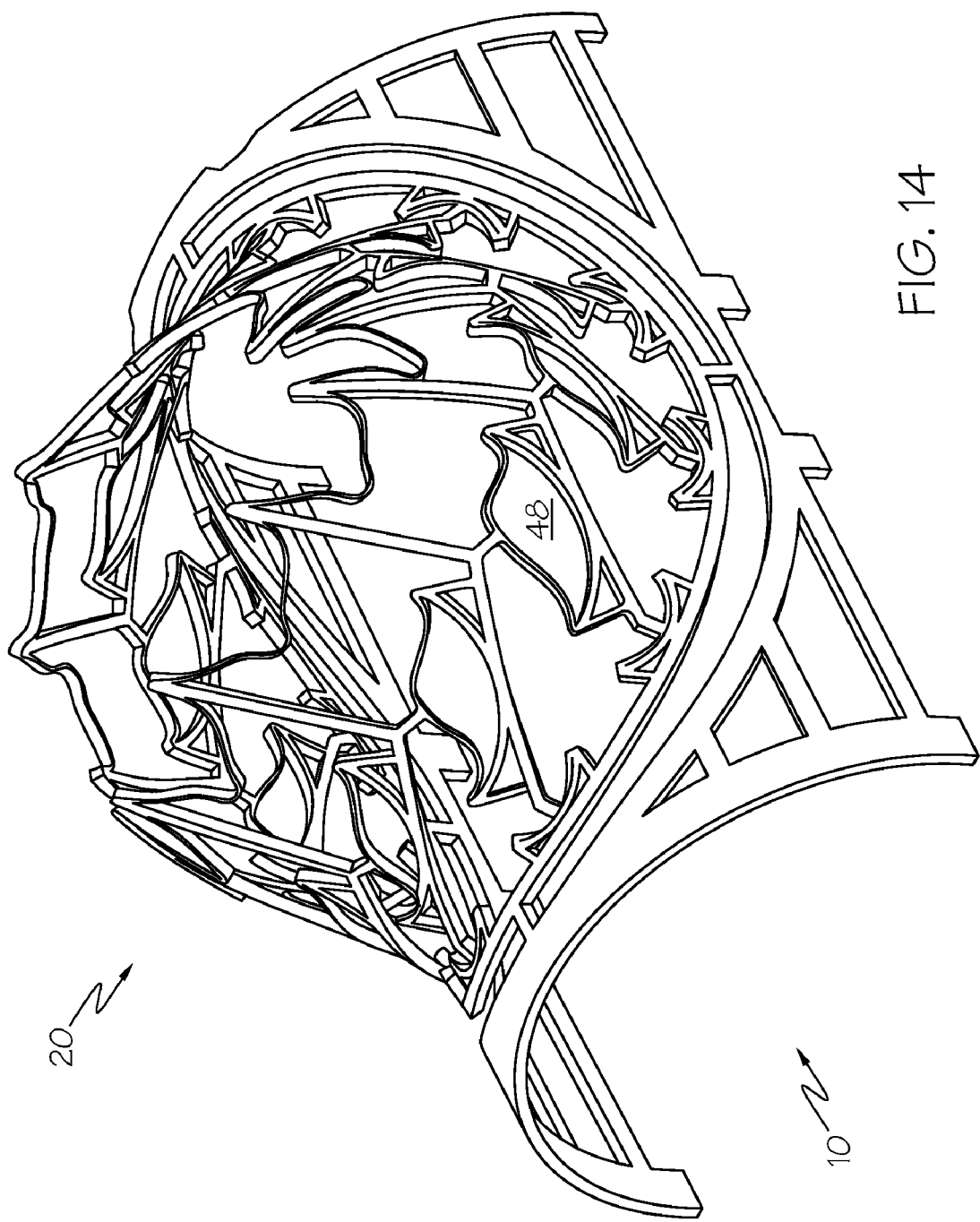

FIG. 14 is a perspective view of the stent portion of FIG. 13 with the side branch a further partially expanded state.

FIG. 15A is a perspective view of the stent portion of FIG. 14 with the side branch in an expanded state, and the bi-stable cells in a second state.

Figure 15B:
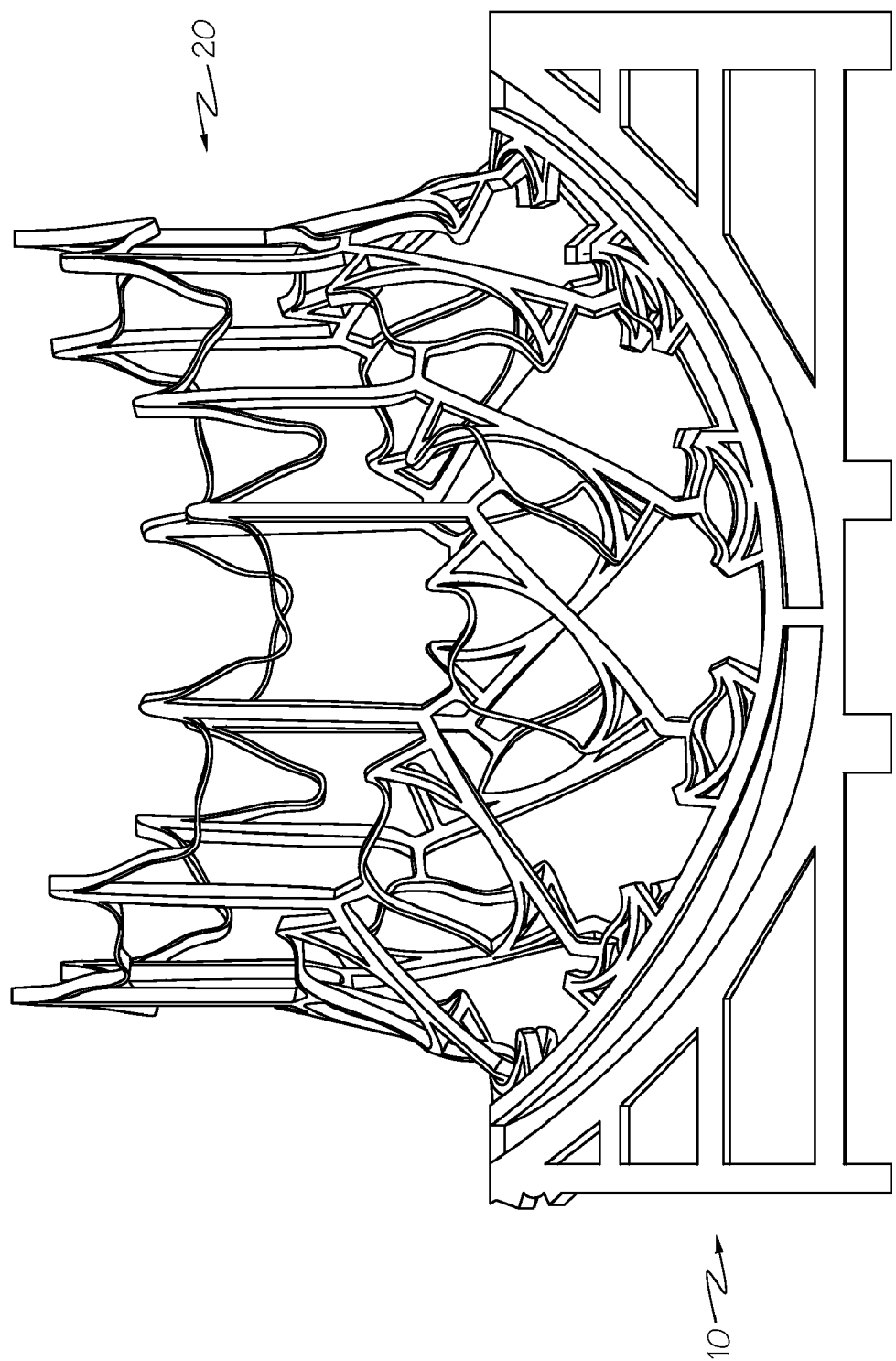

FIG. 15B is a side view of the stent portion of FIG. 14 with the side branch in an expanded state.

Figure 15C:
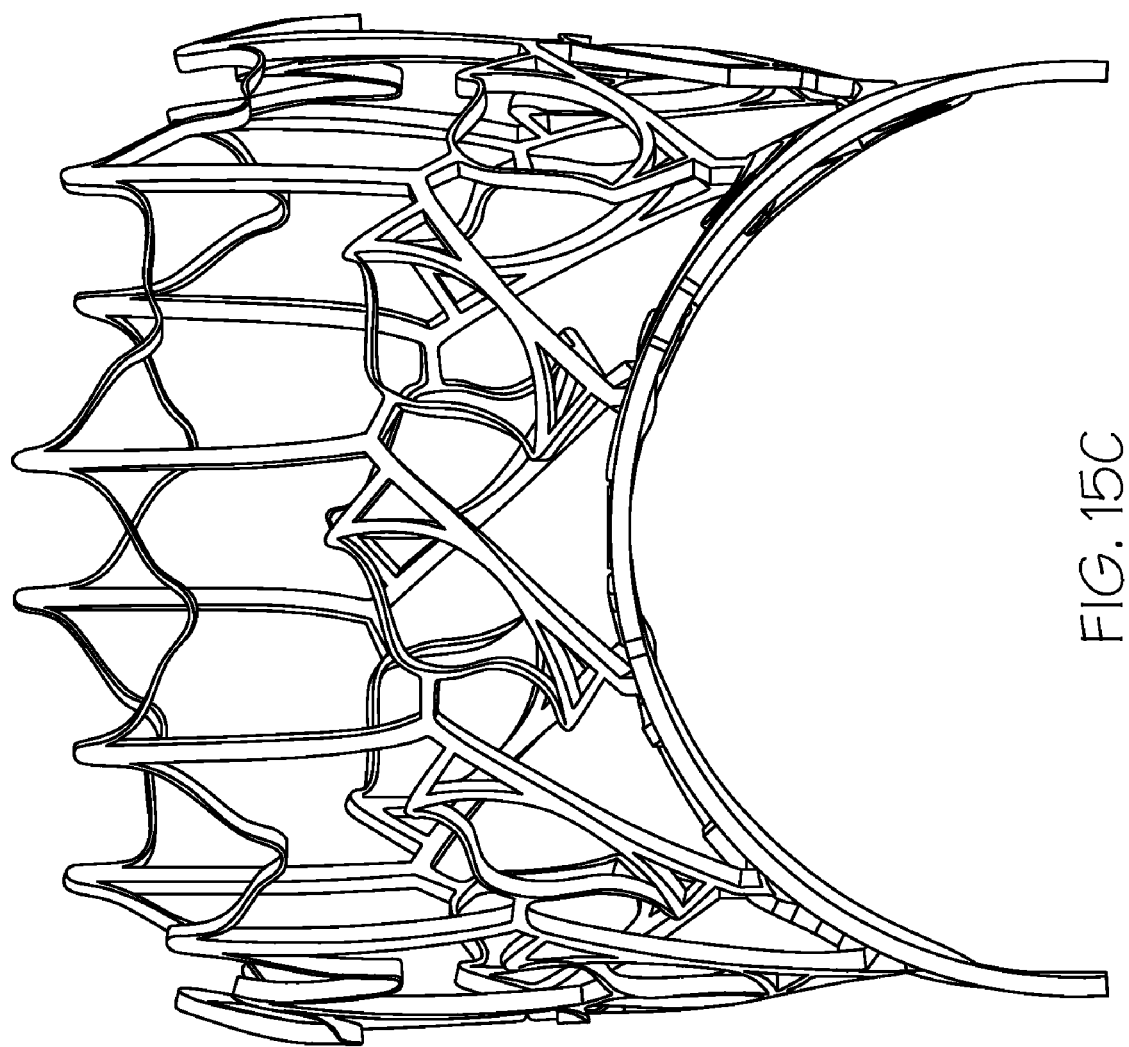

FIG. 15C is an end view of the stent portion of FIG. 14 with the side branch in an expanded state.

Figure 16A:
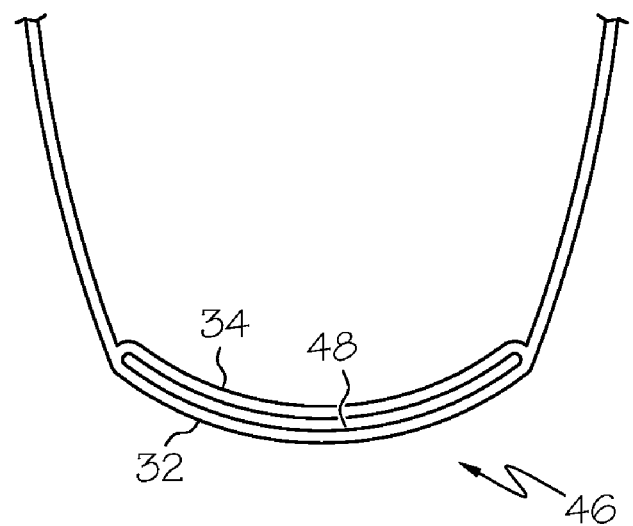

FIG. 16A is an alternative configuration for a petal in a side branch having a cell with at least two stable states/cell geometries, with the cell in a first stable state.

Figure 16B:
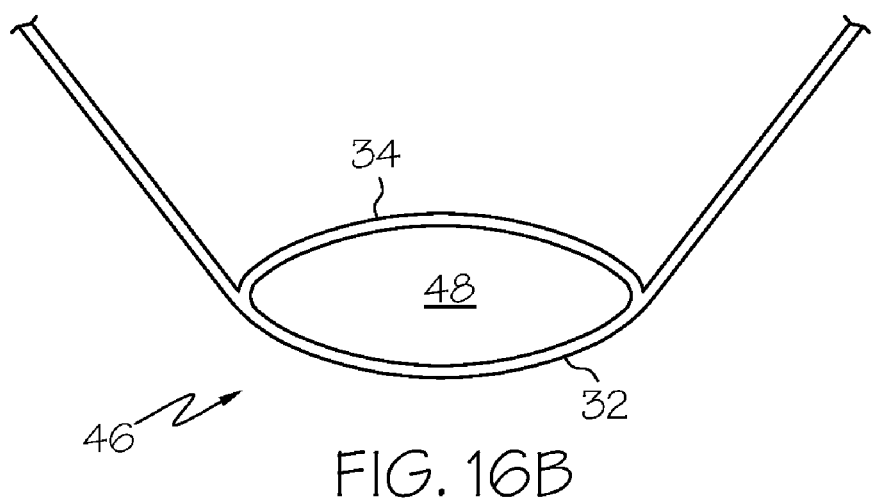

FIG. 16B is the petal of FIG. 16B, with the cell in a second stable state.

Figure 16C:
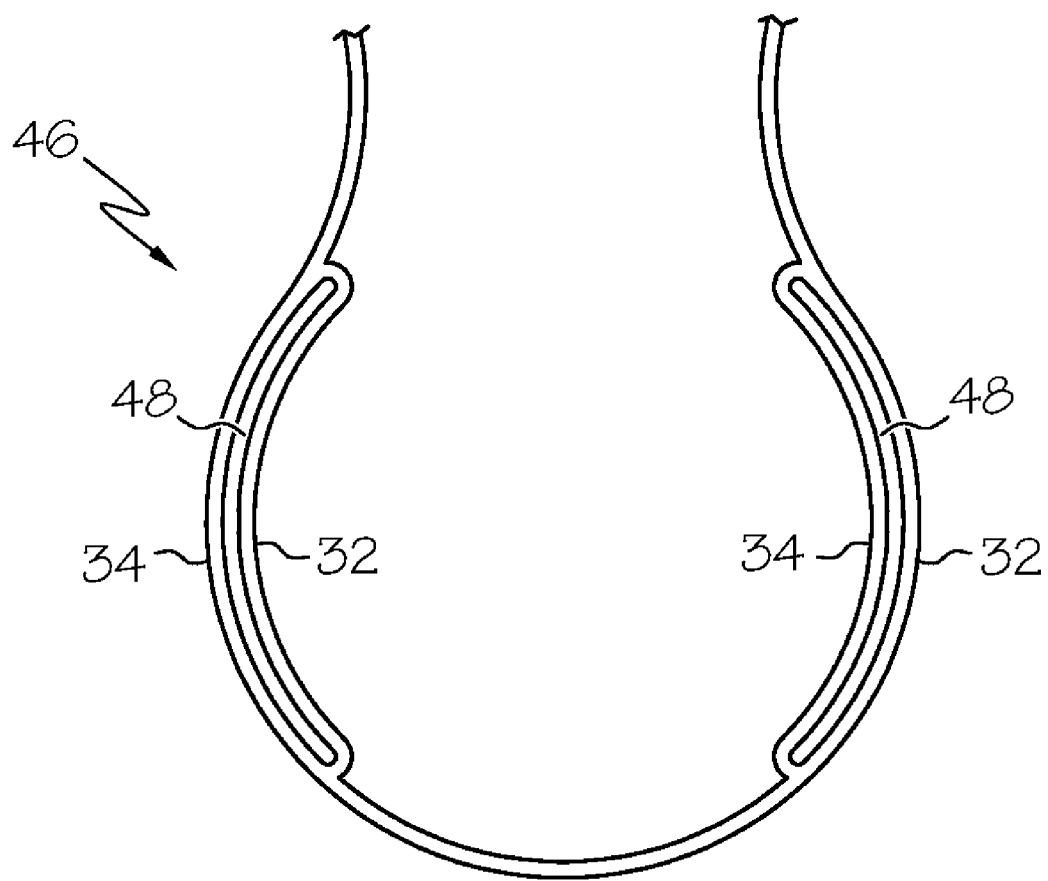

FIG. 16C is a petal with two cells with at least two stable states.

Figure 17:
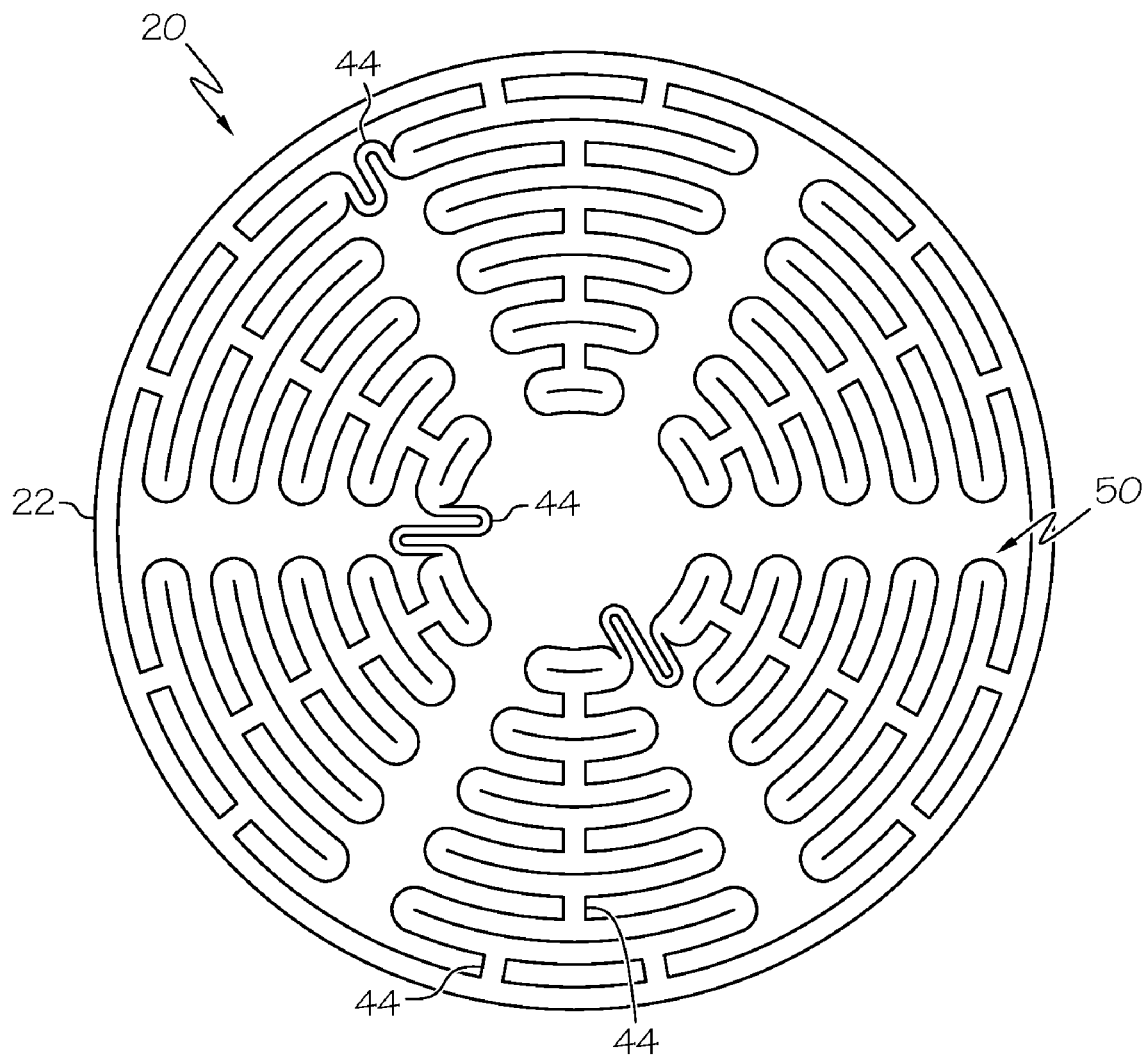

FIG. 17 is a flat view of a side branch configuration having a plurality of the cells with at least two stable states/cell geometries arranged in columns.

Figure 18:
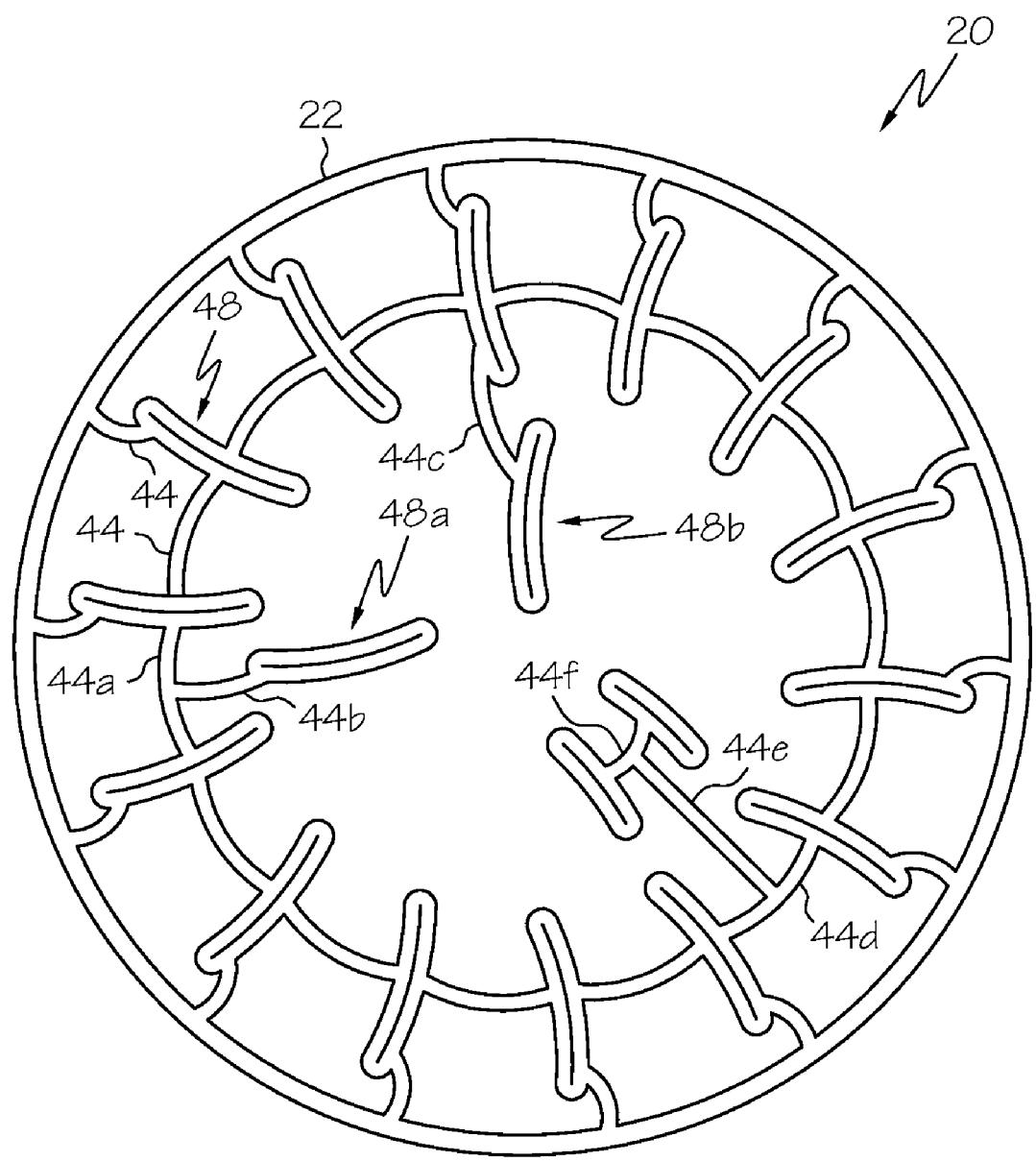

FIG. 18 is a flat view of a side branch configuration having a ring of cells with at least two stable states/cell geometries.

DETAILED DESCRIPTION OF THE INVENTION

While this invention may be embodied in many different forms, there are described in detail herein specific embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

As used herein the term 'stent' refers to an expandable prosthesis for implantation into a body lumen or vessel and includes devices such as stents, grafts, stent-grafts, vena cava filters, expandable frameworks, etc.

As used herein, the term 'bi-stable cell' refers to a cell that has two or more discrete stable configurations, geometries and/or states 36,38. Thus, bi-stable cells includes cells that are multi-stable, i.e. cells with more than two discrete stable configurations.

Referring now to the drawings which are for the purposes of illustrating embodiments of the invention only and not for purposes of limiting same, FIGS. 1-9 show examples of bi-stable cells 48 with different configurations, geometries and/or states. In at least one embodiment, the bi-stable cell 48 has a first stable configuration 36, with a first distance between the first and second cell segments 32, 34 and a first area ($A_1$) defined by the cell segments 32, 34 and a second stable configuration 38 with a second larger distance between the first and second cell segments 32, 34 and second larger area ($A_2$) defined by the cell segments 32, 34.

When a force is applied to the bi-stable cell 48, the bi-stable cell 48 will tend to, or exert a force in the direction of, one of the discrete configurations. In at least one embodiment, the bi-stable cell 48 will tend to one or another of the first and second configurations 36, 38 depending on whether the bi-stable cell 48 has been compressed beyond a transition point. If the bi-stable cell 48 has been compressed beyond the transition point, the bi-stable cell 48 will tend toward a closed configuration, or first state 36. Conversely, if the bi-stable cell 48 has not been compressed to the transition point, the bi-stable cell 48 will tend towards an open configuration or second state 38. As expansive forces are applied to the side branch 20 of the stent 10, the first cell segment 32 and the second cell segments 34 will move away from one another so that the bi-stable cell 48 widens and expands, thereby increasing the area of the bi-stable cell 48.

Thus, the bi-stable cell 48 has an equilibrium position between two stable states, e.g. the first and second states 36, 38. When the force applied to the bi-stable cell 48 exceeds the equilibrium position, the bi-stable cell 48 snaps into one of its stable states depending upon the original state of the bi-stable cell 48 and the direction of the force. Note, that in a bi-stable cell 48, all positions between the stable states, e.g. the first and second states 36, 38, are unstable and can only be maintained by an external force. In a bi-stable cell 48 with more than two stable states, there is an equilibrium position between each stable state. For example, in a bi-stable cell 48 with a first state 36, an intermediate state 37 and a second state 38 there is an equilibrium position between the first state 36 and the intermediate state 37 and an equilibrium position between the intermediate state 37 and the second state 38. Bi-stable cells are also discussed in commonly assigned application Ser. No. 11/368,913, entitled Non-Foreshortening Sheaths and Assemblies for Use, hereby incorporated by reference in its entirety.

Figure 1A:
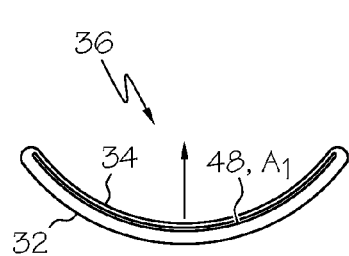
FIG. 1A is view of a configuration of a cell that has a bi-stable geometry, with the cell in a first stable state.
Figure 1B:
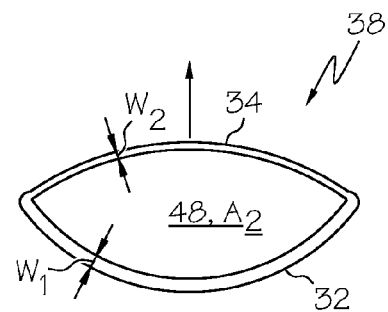
FIG. 1B is a view of the cell in FIG. 1A in a second stable state.
Figure 2A:
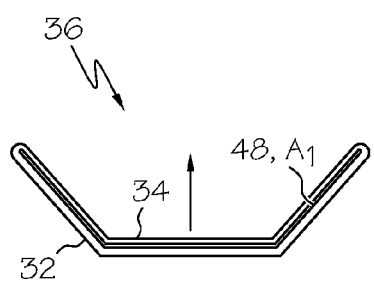
FIG. 2A is a view of another configuration of a cell that has a bi-stable geometry, with the cell in a first stable state.
Figure 2B:
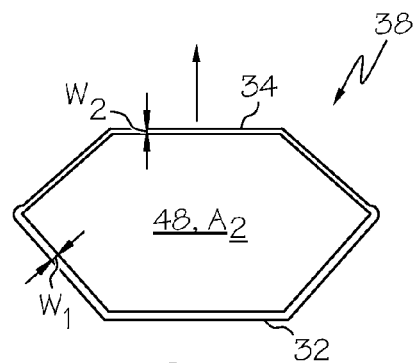
FIG. 2B is a view of the cell in FIG. 2A in a second stable state.

As shown, for example in FIGS. 1A and 1B, the bi-stable cell 48 is defined by at least one first cell segment 32 and at least one second cell segment 34 which are constructed and arranged so that the second cell segment 34 is more flexible, weaker, or less rigid, than the first cell segment 32, so that the second cell segment 34 can assume different stable positions and provide the bi-stable cell 48 with at least two stable states. In at least one embodiment, the first cell segment 32 has a greater width ($W_1$) than the second cell segment 34 ($W_2$) as shown in FIGS. 1B and 2B. As used in this application, the width of a member, e.g. the first cell segment 32, is measured along the outer surface of the stent. In some embodiments, the first cell segment 32 is more rigid than the second cell segment 34. In other embodiments, the first cell segment 32 is stronger than the second cell segment 34. The strength and rigidity of the cell segments 32, 34 can be changed by using different materials for the second cell segment 34 than for the first cell segment 32 or by treating one cell segment 32, 34 differently than the other cell segment 32, 34. For example, some materials can be strengthened by heat treatment. Thus, in this embodiment, the first cell segment 32 would be heat treated so that it would be stronger than the second cell segment 34. Some materials, such as Nitinol, for example, become more pliable or less rigid when heated. Thus, if the cell segments 32, 34 are made from Nitinol, the second cell segment 34 would be heat treated so that it would be less rigid than the first cell segment 32.

Note that the first and second cell segments 32, 34 can have any length. The length and/or the configuration of the first and second cell segments 32, 34 affects the area of the bi-stable cell 48 in both the first and second states 36, 38. The bi-stable cell 48 has a first area ($A_1$) in the first state 36, a second area ($A_2$) in the second state 38 and the first area ($A_1$) is smaller than the second area ($A_2$).

Each cell segment 32, 34 has a length. If the cell segment 32, 34 is not straight, the length is the pathway from one end of the cell segment 32, 34 to the second end of the cell segment 32, 34. As shown in FIGS. 1A and 1B, the length of the first cell segment 32 is the same as the length of the second cell segment 34. In some embodiments, the length of the first cell segment 32 is different than the length of the second cell segment 34, as shown for example in FIGS. 9A and 9B.

In some embodiments, the first and second cell segments 32, 34 have the same configuration in the first state 36 and in the second state 38, as shown, for example, in FIGS. 1A and 1B. In this embodiment, the first and second cell segments have a curvilinear configuration. As shown in FIG. 1A, the first and second cell segments 32, 34 have the same configuration and the same orientation relative to the longitudinal axis of the stent in the first state 36. Thus, the first cell segment 32 and the second cell segment 34 can be described as having complementary shapes in the first state 36. Alternatively, the first and second cell segments 32, 34 can be described as being parallel to one another in the first state 36. In FIG. 1B, the first and second cell segments 32, 34 have the same configuration, but opposite orientations relative to the longitudinal axis of the stent in the second state 38.

Figure 3A:
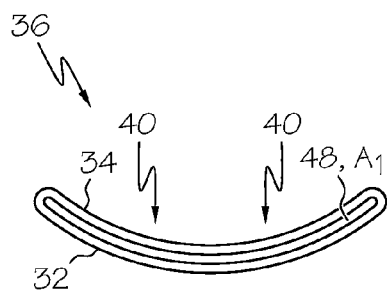
FIG. 3A is a view of a configuration of a cell with at least one hinge that has at least two stable states/cell geometries, with the cell in a first stable state.
Figure 3B:
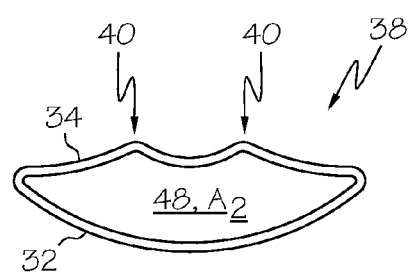
FIG. 3B is a view of the cell in FIG. 3A in a second stable state.

In other embodiments, the first and second cell segments 32, 34 have the same configuration in the first state 36 and different configurations in the second state 38, as shown, for example, in FIGS. 3A and 3B. In this embodiment, the first cell segment 32 has the same configuration in the first and second states 36, 38 and the second cell segment 32 has a first configuration in the first state 36 and a second configuration in the second state 38, where the first and second configurations are different. In FIGS. 3A and 3B, the first and second cell segments 32, 34 have the same curvilinear configuration in the first state 36 and different curvilinear configurations in the second state 38.

Figure 7A:
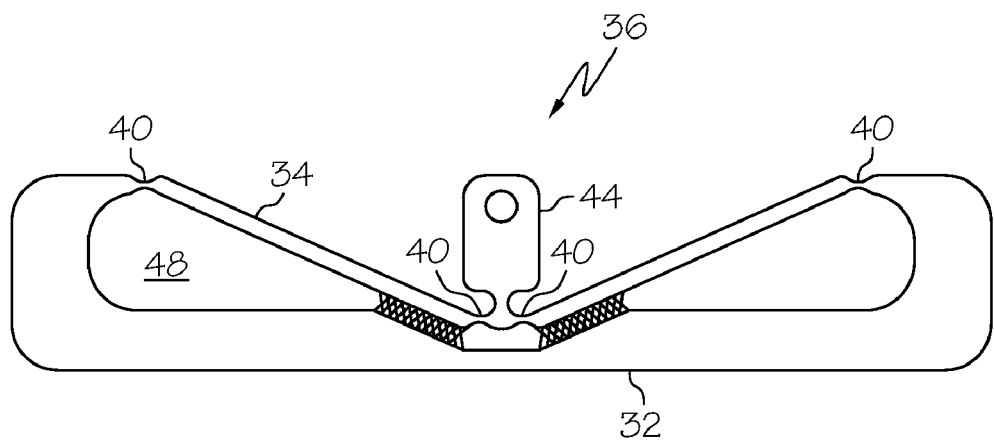
FIG. 7A is a view of a configuration of a cell that has a bi-stable geometry with built in hinge points, with the cell in a first stable state.
Figure 7B:
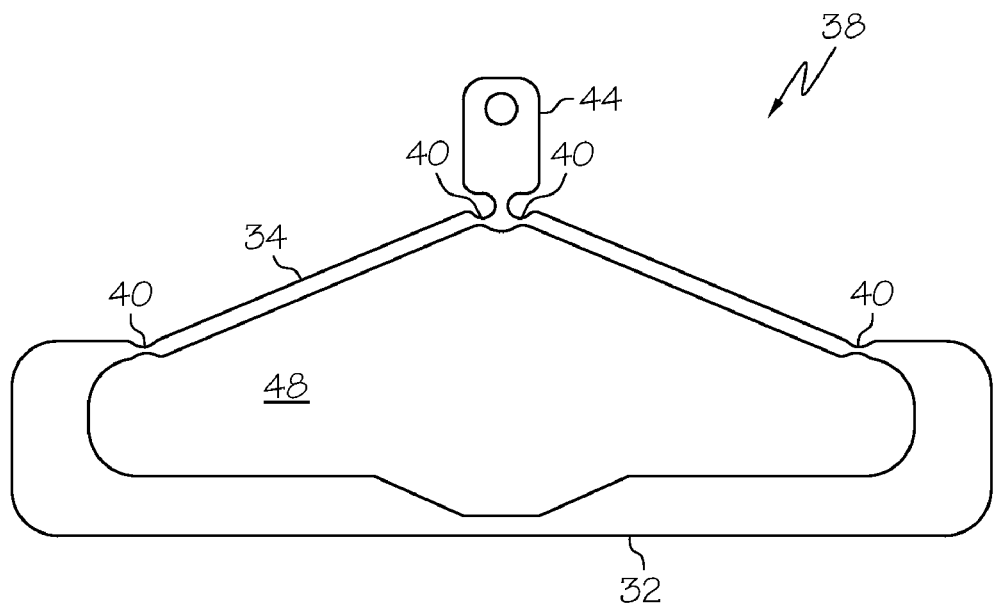
FIG. 7B is a view of the cell in FIG. 7A in a second stable state.

In some embodiments, the first and second cell segments 32, 34 have different configurations in both the first and second states 36, 38. For example, as shown in FIGS. 7A and 7B, the first and second cell segments 32, 34 have different configurations in the first state 36 and the second state 38. In at least one embodiment, the first cell segment 32 has the same configuration in both the first state 36 and in the second state 38. As shown in FIG. 7A, portions of the first cell segment 32 and portions of the second cell segment 34 are complementary to one another in the first state 36, as shown by hatch marks. Thus, in this embodiment, unlike FIG. 1A, only a portion of the first and second cell segments 32, 34 are complementary to one another in the first state 36 instead of the entire first and second cell segments 32, 34 being complementary.

The shape of the first and second cell segments 32, 34 and the relationship of the first and second cell segments 32, 34 to one another determines the configuration or cell geometry of the bi-stable cell 48. As shown in the figures, the cell geometry of the bi-stable cell 48 is different in the first and second states 36, 38. Thus, the bi-stable cell 48 has a first stable cell geometry in the first state 36 and a second stable cell geometry in the second state 38 and the first and second stable cell geometries are different from one another.

For example, in FIGS. 1A and 1B, the first stable cell geometry of the bi-stable cell 48 is a curvilinear configuration and the second stable cell geometry of the bi-stable cell 48 is an oval shaped or eye shaped configuration. Similarly, in FIGS. 2A and 2B, the first stable cell geometry of the bi-stable cell 48 is an angular C shaped configuration and the second stable cell geometry of the bi-stable cell 48 is a polygonal or hexagonal shaped configuration. The first stable cell geometry in FIG. 2A can also be described as a boat shaped configuration.

Figure 4A:
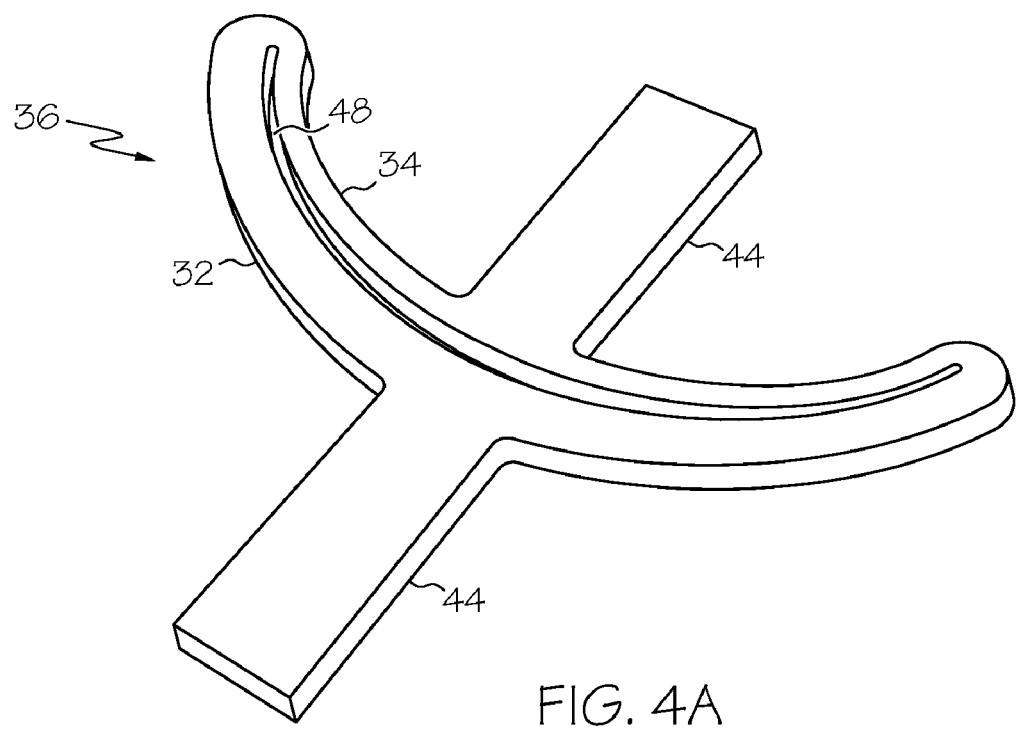
FIG. 4A is a view of a configuration of a cell that has a bi-stable geometry with two connectors, with the cell in a first state.
Figure 4B:
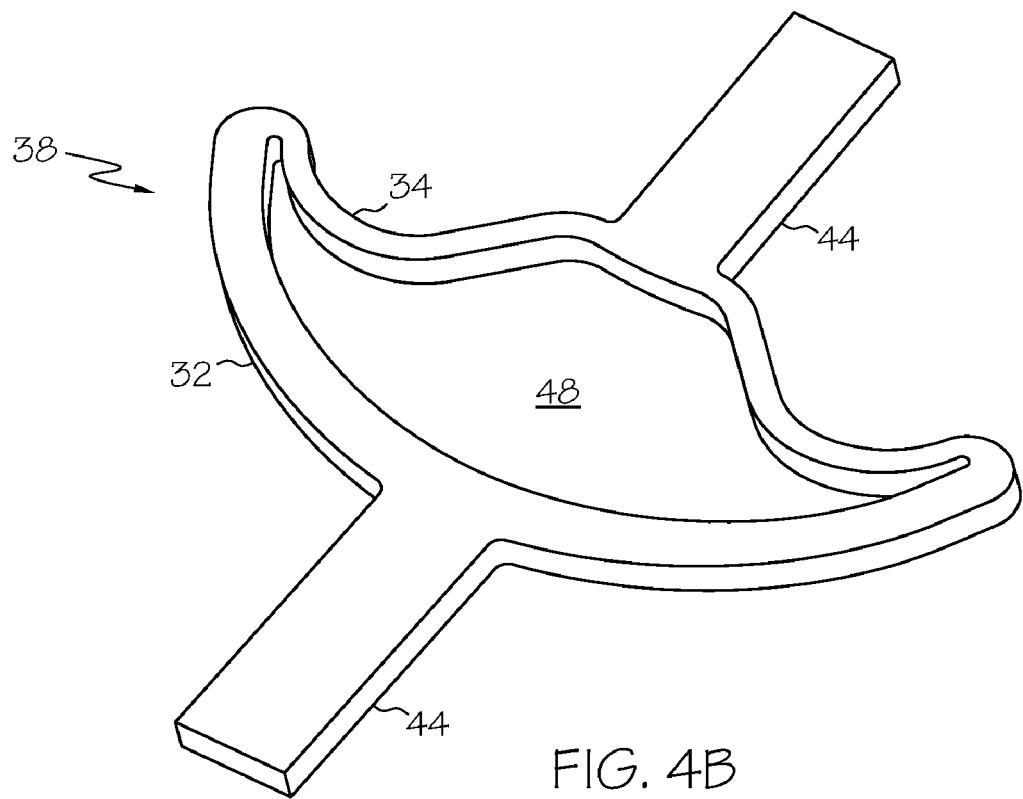
FIG. 4B is a view of the cell in FIG. 4A in a second stable state.

Other examples of different stable cell geometries in the first and second states 36, 38 are shown in FIGS. 3A-B, 4A-B and 7A-B. In the bi-stable cell 48 embodiments of FIGS. 3-4, the first stable cell geometry of the bi-stable cell 48 is a curvilinear configuration and the second stable cell geometry of the bi-stable cell 48 is a symmetrical configuration. Note that the symmetrical configurations or cell geometries in FIG. 3B and 4B are different due to the different configurations of the second cell segment 34 in the second state 38. The cell geometry of FIG. 3B is cape shaped whereas the cell geometry of FIG. 4B is hat shaped. The bi-stable cell 48 embodiment in FIG. 7 has a first stable cell geometry in the form of a "wing" configuration and a second stable cell geometry that is triangular shaped.

In at least one embodiment, shown for example, in FIGS. 3A, 3B, 7A-B, 8A-C, the second cell segment 34 and/or the first cell segment 32 has at least one hinge 40. It is within the scope of the invention for either or both of the first and second cell segments 32, 34 to have one, two, three, four, five, six or more hinges 40 along the length of the cell segment 32, 34. In at least one embodiment, the hinges 40 are deformable. In some embodiments, the hinges 40 are elastically deformable. In other embodiments, the hinges 40 are plastically deformable. In some embodiments, the hinges 40 are regions in the cell segment 32, 34 that have a smaller width than the adjacent regions of the cell segment 32, 34.

In at least one embodiment, a bi-stable cell 48 defined by at least one cell segment 32, 34 having hinges 40 has more than two stable states, 36, 37, 38. For example, the bi-stable cell 48 shown in FIG. 8A-D has two different intermediate stable states 37a,b. The second cell segment 34 can be described as having a proximal section, a middle section and a distal section. In the intermediate stable state 37a,b embodiments, one of the proximal section or the distal section stays in the first stable state 36 position while the other is in the second stable state 38 position, with the middle section extending between the proximal and distal sections at an oblique angle. An oblique angle, as used in this application is any angle between 0 and 90 degrees and 90 and 180 degrees and a perpendicular angle is a 90 degree angle.

Figure 8A:
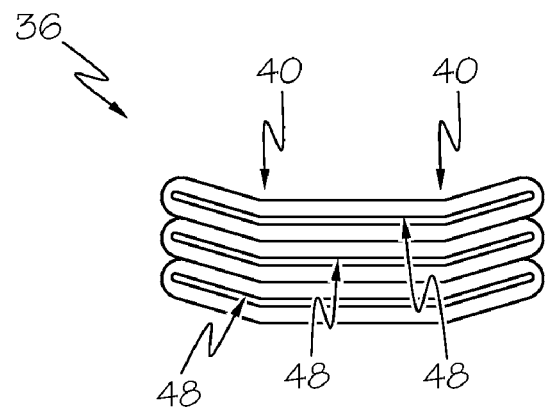
FIG. 8A is a view of a column of bi-stable cells that have at least two stable states/cell geometries engaged to one another, with the bi-stable cells in a first stable state.
Figure 8D:
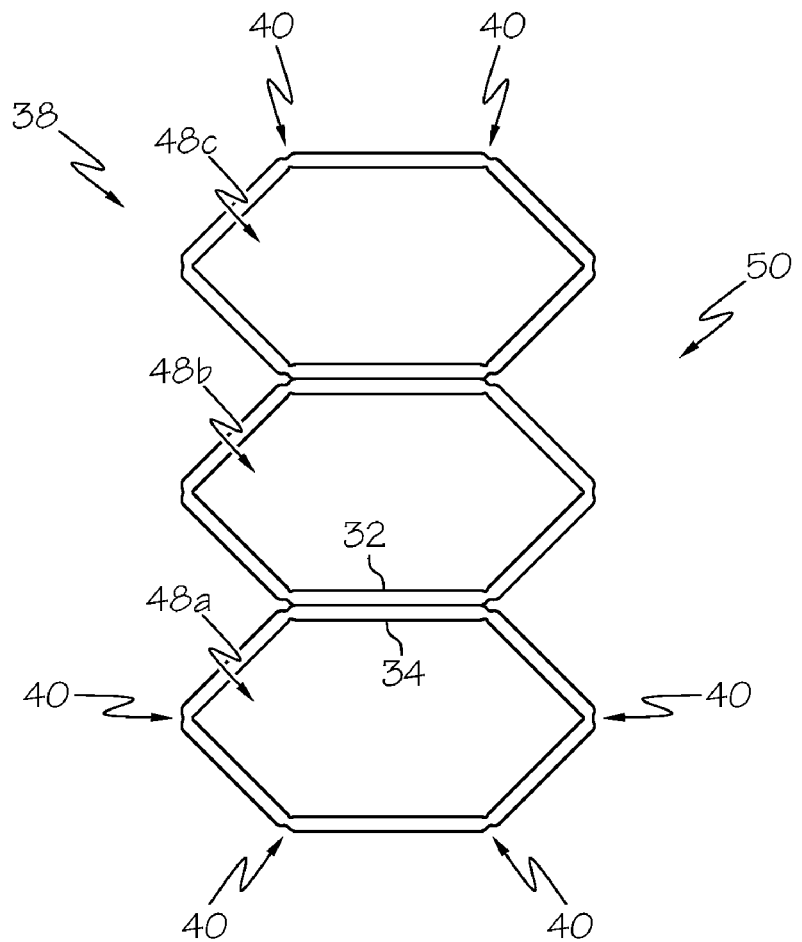
FIG. 8D is a view of the column of cells in FIG. 8A in a second stable state.

Thus, in this embodiment, the bi-stable cell 48 has more than two stable cell geometries. The bi-stable cell 48 has a first state 36 cell geometry, two different intermediate state cell geometry embodiments 37a,b and a second state cell geometry 38. Similar to FIG. 2A, the bi-stable cell 48 in FIG. 8A has first state cell geometry that is an angular C-shaped configuration. Note that the lengths of the proximal and distal sections of the second cell segment 34 and their angle to the middle section in FIGS. 2 and 8 are different, which results in angular C-shaped configurations or boat shaped configurations that are different from one another. As shown in FIGS. 8B-C, the bi-stable cell 48 has cell geometry that is an irregular configuration in both of the intermediate states 37a,b. The bi-stable cell 48 in FIG. 8D has the same cell geometry in the second state 38 as the bi-stable cell 48 in FIG. 2B, namely a hexagonal or polygonal configuration.

Figure 5:
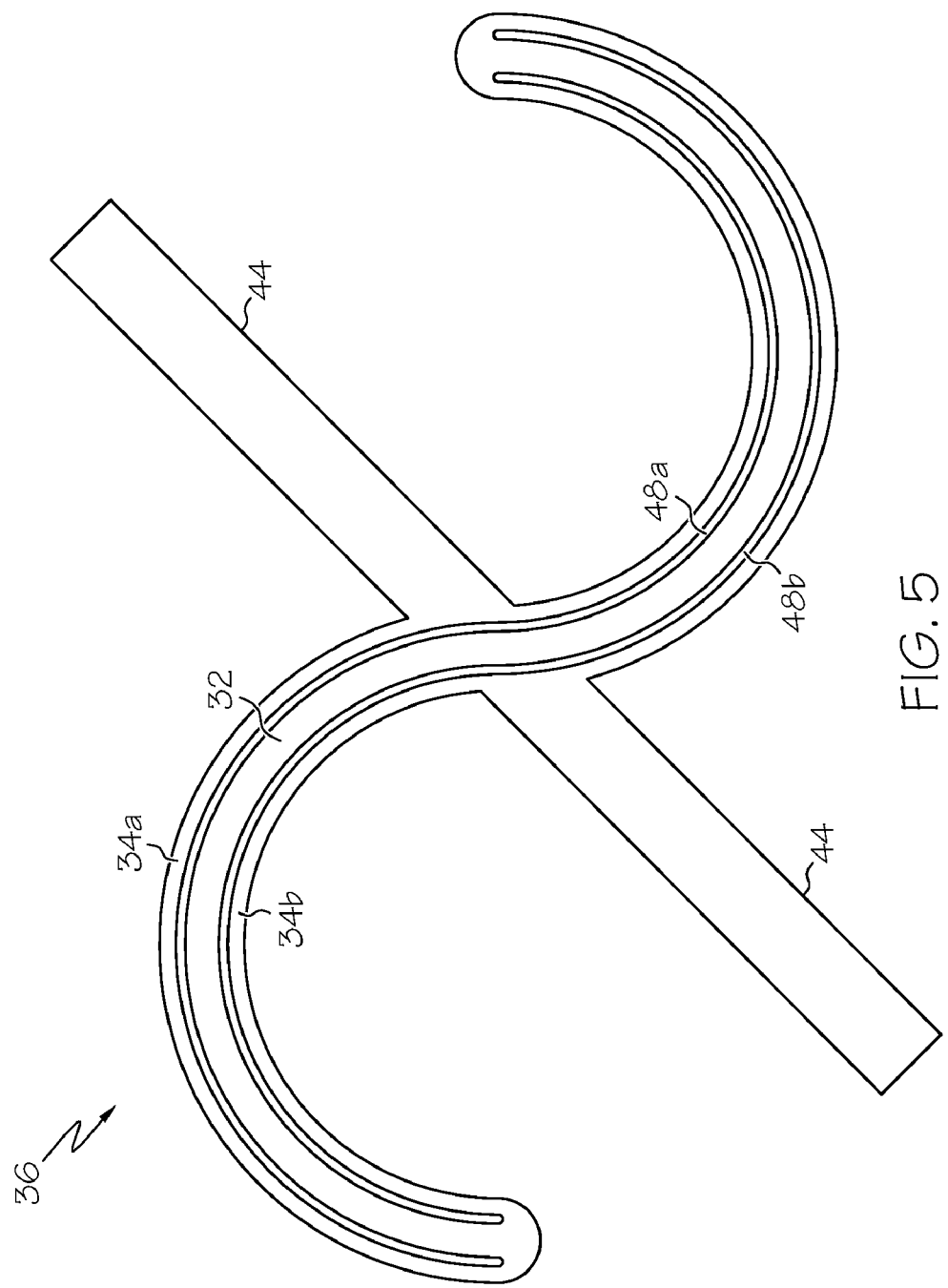
FIG. 5 is a view of a configuration of a cell that has double bi-stable geometry and off center connectors to open the cell, with the cells in the first state.
Figure 6:
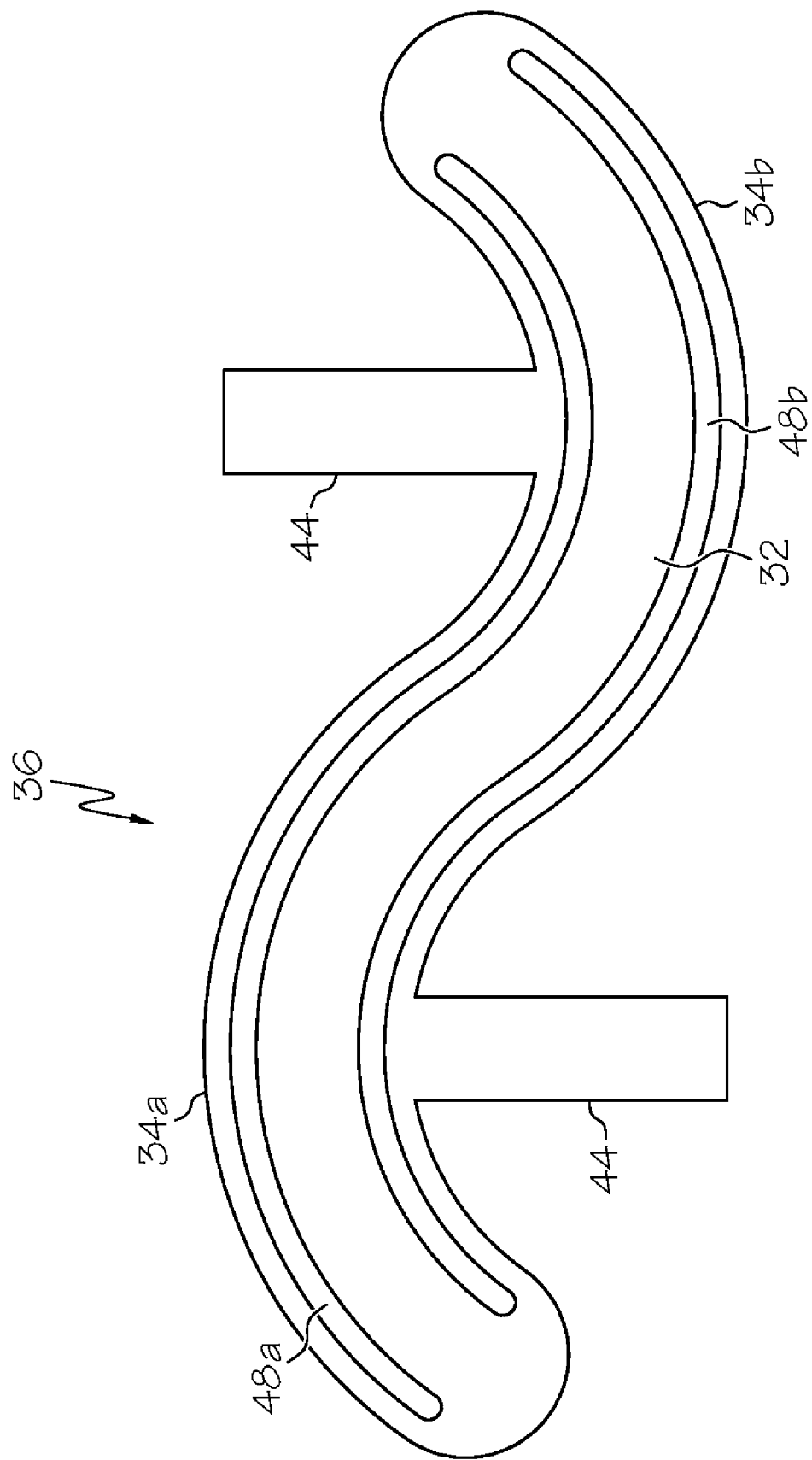
FIG. 6 is a view of a configuration of a cell that has double bi-stable geometry, with the cells in the first state.

In at least one embodiment, members of the stent 10 are arranged to form a double bi-stable cell, as shown, for example, in FIGS. 5 and 6. A double bi-stable cell geometry comprises one first cell segment 32 and two second cell segments 34a,b arranged so that the first cell segment 32 is positioned between the two second cell segments 34a,b. Note that as with the bi-stable geometry, the first cell segment 32 is wider than both of the second cell segments 34a,b. The first cell segment 32 and second cell segment 34a define a first cell 48a and the first cell segment and second cell segment 34b define a second cell 48b. As shown in FIGS. 5 and 6, the first cell segment 32 and the second cell segments 34a,b have an S-shaped configuration. The configurations of the first and second cell segments 32, 34 in FIGS. 5 and 6 can also be described as curvilinear or sinusoidal.

In some embodiments, the first cell 48a and the second cell 48b have the same configuration in both the first state 36 and the second state 38. In other embodiments, the first cell 48a and the second cell 48b have the same configuration in the first state 36 and different configurations in the second state 38. One example of this embodiment, is if the first cell 48a has a configuration like FIG. 1 and the second cell 48b has a configuration like FIG. 3. Both cells in FIG. 1A and 3A have the same configuration in the first state 36 but different configurations in the second state 38.

In at least one embodiment, a connector 44 is engaged to the first cell segment 32 and/or the second cell segment 34. In at least one embodiment, the connectors 44 aid in the transition of the bi-stable cell from the first state 36 to the second state 38. In some embodiments, the connectors 44 open the bi-stable geometry by a twisting motion. In other embodiments, the connectors 44 open the bi-stable geometry due to the tension the connectors 44 exert on the second cell segment 34. In some embodiments, both second cell segments 34a,b of a double bi-stable cell transition to the second state 38. In other embodiments, only one of the second cell segments of a double bi-stable cell transitions to the second state 38.

In FIGS. 5 and 6 a connector 44 is engaged to both second cell segments 34a,b, although the connectors 44 are engaged to different positions along the lengths of the second cell segments 34a,b. In FIG. 5, the connectors 44 are engaged to a middle region of the second cell segments 34a,b. Similarly, the connectors 44 in FIGS. 4A and 4B are engaged to the middle region of the first and second cell segments 32, 34. In FIGS. 4 and 5, the connectors 44 are positioned on the same axis. In FIG. 4, the connectors 44 are perpendicular to the first and second cell segments 32, 34 while in FIG. 5, the connectors 44 are at an oblique angle to the first and second cell segments 32, 34. In FIG. 6, the connectors 44 are engaged toward the end regions of the second cell segments 34a,b. As shown in FIG. 6, the two connectors 44 are parallel to one another but it is within the scope of the invention for the connectors 44 to be at oblique angles to one another.

In some embodiments, bi-stable cells 48 are engaged to one another to form of columns 50 of bi-stable cells 48, as shown, for example, in FIGS. 8A-9B. The configurations of the bi-stable cells 48 forming the column 50 of bi-stable cells 48 in FIGS. 8A-9B are merely examples of possible configurations. It is within the scope of the invention for the bi-stable cells 48 forming a column 50 of bi-stable cells 48 to have any configuration. In some embodiments, the bi-stable cells 48 in the column 50 of bi-stable cells 48 have the same configuration. In other embodiments, at least one of the bi-stable cells 48 in a column 50 of bi-stable cells 48 has a different configuration than the other bi-stable cells 48. In some embodiments, the bi-stable cells 48 are aligned with one another as shown, for example, in FIG. 8D. In other embodiments, the bi-stable cells 48 are offset from one another, as shown, for example, in FIG. 8E.

Figure 9A:
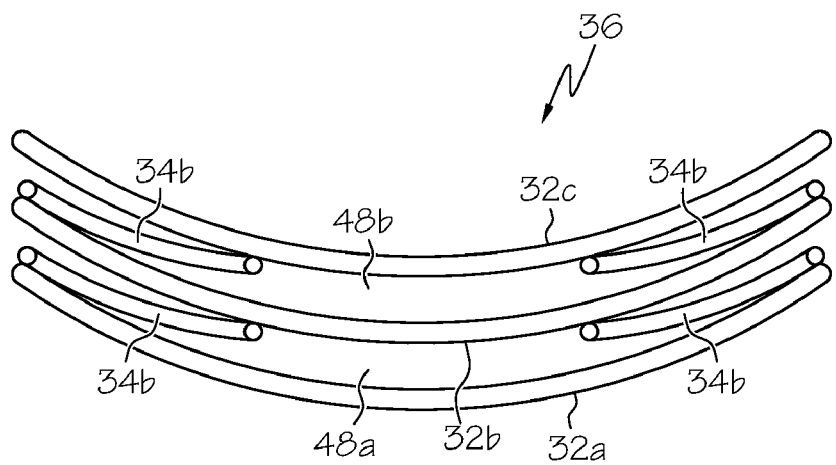
FIG. 9A is a view of a configuration of cells that have at least two stable states/cell geometries, with the cells in a first stable state, where two adjacent cells are partially defined by a common cell segment.
Figure 9B:
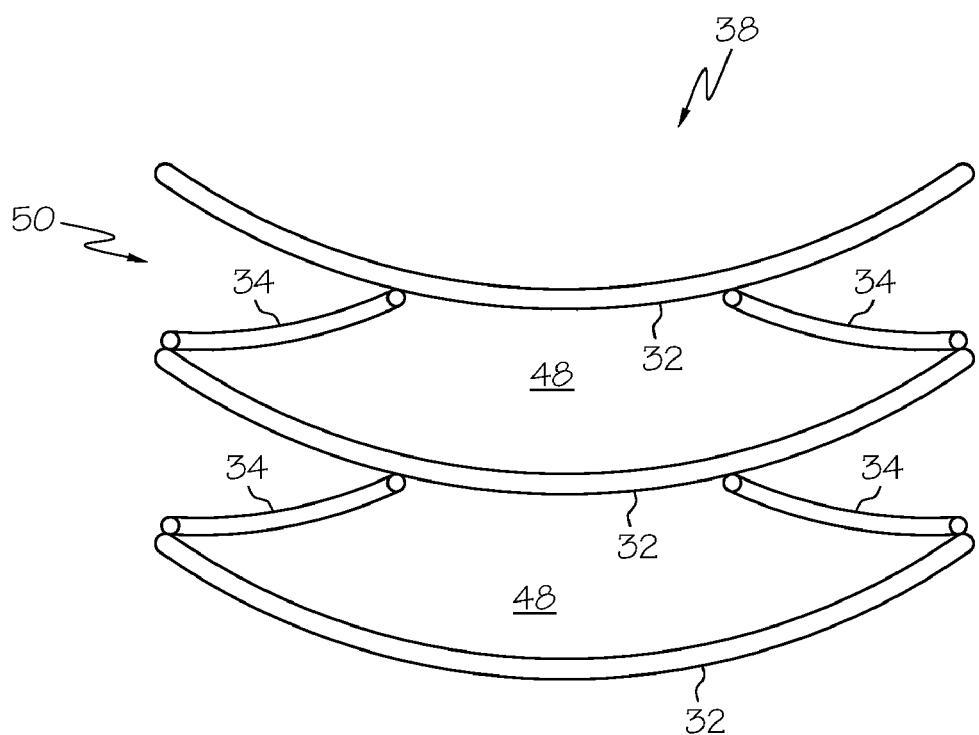
FIG. 9B is a view of the cells in FIG. 9B in a second stable state.

In some embodiments, adjacent bi-stable cells 48 are directly engaged, as shown in FIGS. 8D and 9B, so that the second cell segment 34 of a first bi-stable cell 48a is engaged to the first cell segment 32 of a second bi-stable cell 48b. As shown in FIG. 8D, the entire length of the first and second cell segments 32, 34 are engaged to one another. However, it is within the scope of the invention for portions of the first and second cell segments 32, 34 to be engaged to one another. In FIGS. 9A and 9B, the first bi-stable cell 48a is engaged to the second bi-stable cell 48b by two second cell segments 34a. In this embodiment, the bi-stable cell 48a is defined by first cell segment 32a, two second cell segments 34a and first cell segment 32b.

In other embodiments, adjacent bi-stable cells 48 in a column 50 of bi-stable cells 48 are engaged by a connector 44, for example as shown in FIGS. 8E and 17. In at least one embodiment, the size/area of the bi-stable cells 48 in a column 50 of bi-stable cells 48 is the same. In at least one embodiment, the bi-stable cells 48 in a column 50 of bi-stable cells 48 have different sizes/area. Thus, the size/area of the bi-stable cells 48 in a column 50 of bi-stable cells 48 can sequentially decrease as shown, for example, in the side branch 20 of FIG. 17, to form a tapered column 50 of bi-stable cells 48.

Because any suitable stent geometry may be used for the tubular body of the stent 10, many figures only show the side branch 20 of the stent 10 without any structure, or only a small portion of structure, shown for the rest of the tubular body of the stent 10. It is understood that any suitable structure may be employed for the tubular body of the stent 10 including, but not limited to, the cellular patterns, shown by way of example only, in FIG. 12, U.S. Pat. Nos. 6,835,203, 6,348,065, and 6,013,091. Although, the bi-stable cell embodiments described in FIGS. 1-9 are discussed in reference to a side branch of a stent, it is within the scope of the invention for the bi-stable cell embodiments described herein to be used in the stent geometry of the tubular body of the stent. The tubular body of the stent can comprise only bi-stable cells or can comprise both bi-stable cells and cells that are not bi-stable cells, i.e. cells that have only one stable state, for example, cells 49 in FIG. 17.

Figure 10A:
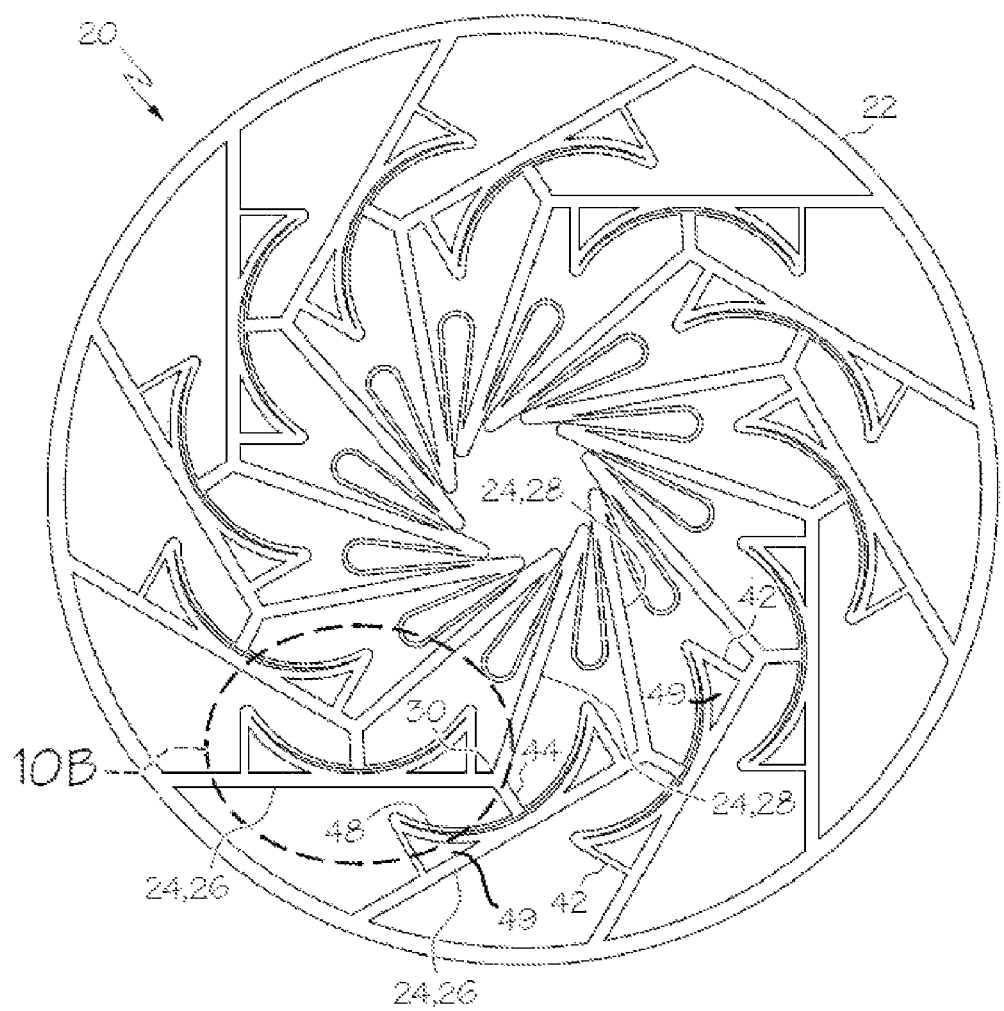
FIG. 10A is a flat view of a side branch configuration with a plurality of cells with at least two stable states/cell geometries, with the cells in a first stable state.
Figure 10B:
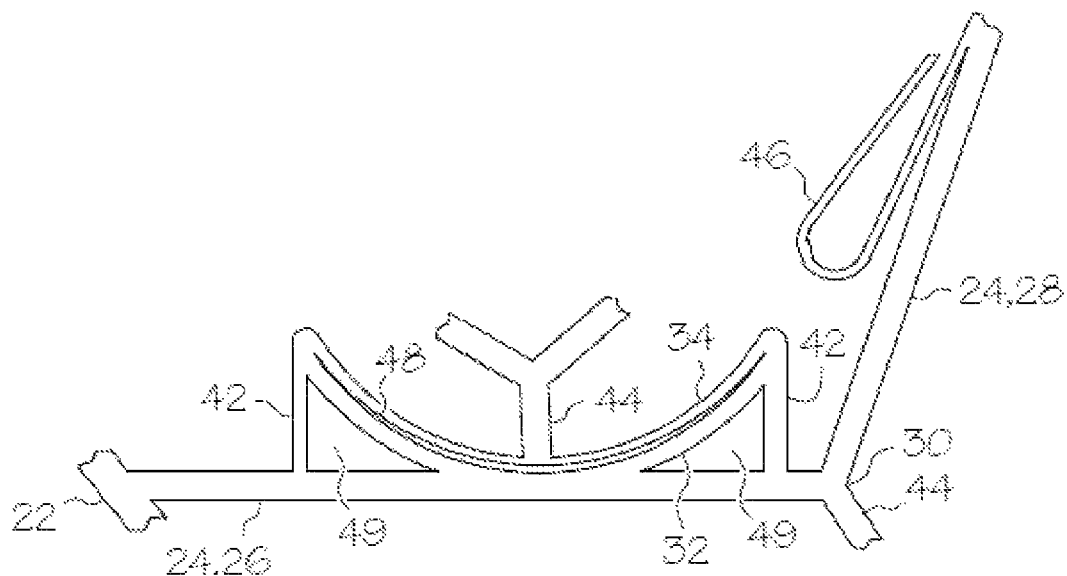
FIG. 10B is an enlarged view of a portion of the side branch in FIG. 10A.

One skilled in the art will recognize that the bi-stable cell geometries shown in FIGS. 1-9B can be incorporated into a side branch 20 in many different ways, some examples of which are provided hereinafter. FIG. 10A is a flat view of a non-limiting example of a configuration for a side branch 20 that has a plurality of bi-stable cells 48a and a plurality of cells 49 with one stable state. FIG. 10B is an enlarged view of a portion of the side branch 20 of FIG. 10A. Note that although the bi-stable cell 48 configuration shown in FIGS. 1A and 1B In the side branch 20 configuration shown in FIGS. 10A-C and 11A-B, the bi-stable cell 48 has the configuration shown in FIGS. 1A and 1B, but, as discussed above, it is within the scope of the invention for the bi-stable cell 48a to have any configuration.

Figure 11A:
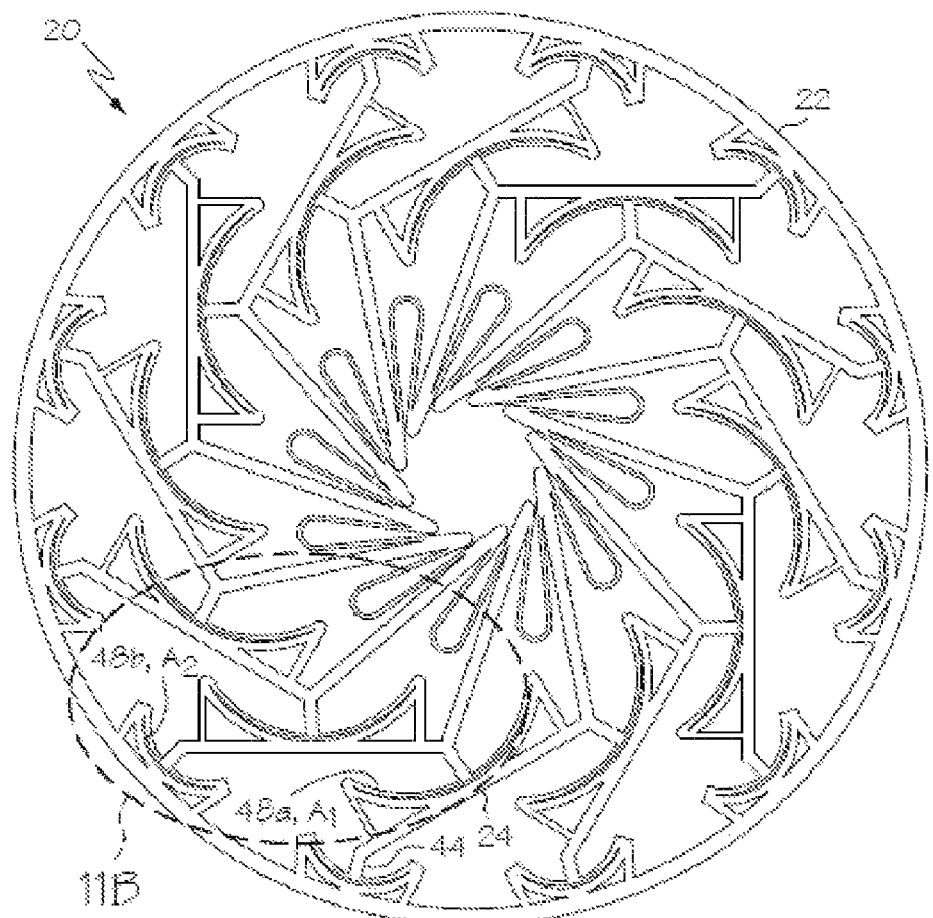
FIG. 11A is a flat view of another side branch configuration with a plurality of cells with at least two stable states/cell geometries, with the cells in a first stable state.
Figure 11B:
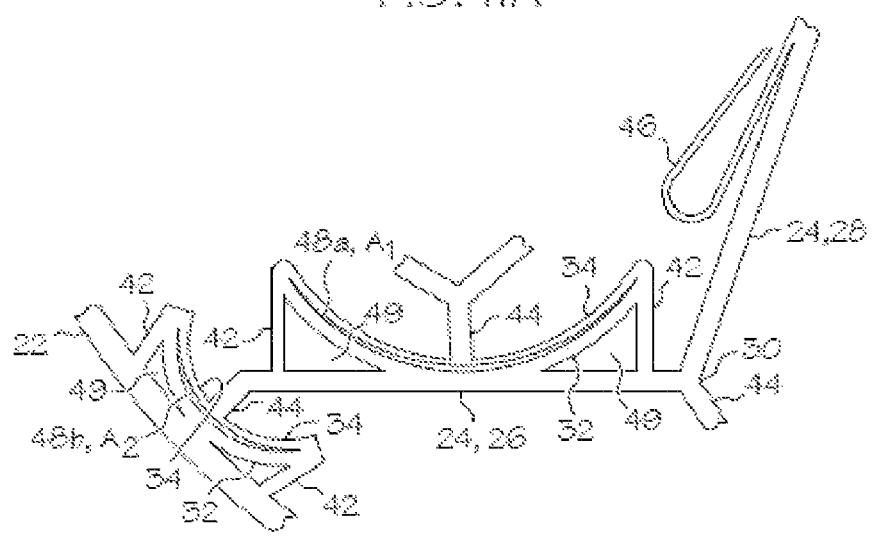
FIG. 11B is an enlarged view of a portion of the side branch in FIG. 11A.

It is also within the scope of the invention for the side branch 20 to have bi-stable cells 48 which define different areas in the first state 36 and/or different area in the second state 38. For example, the side branch 20 in FIG. 11A has a plurality of bi-stable cells 48a with a first area ($A_1$) and a plurality of bi-stable cells 48b with a second area ($A_2$), where the first area ($A_1$) is larger than the second area ($A_2$). In some embodiments, the first area ($A_1$) is greater than the second area ($A_2$) in both the first and second states 36, 38. As shown in FIGS. 11A and 11B, the lengths of the first and second cell segments 32, 34 of the bi-stable cells 48a with the first area ($A_1$) are greater than the lengths of the first and second cell segments 32, 34 of the bi-stable cells 48b with the second area ($A_2$).

The side branch 20 in FIG. 10A has twelve bi-stable cells 48, while the side branch 20 in FIG. 11A has twenty-four bi-stable cells 48. A side branch 20 can have any number of bi-stable cells 48, thus, it is within the scope of the invention for a side branch 20 to have one, two, three, four, five, six, seven, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty or more bi-stable cells 48.

As shown in FIG. 10A, the side branch 20 comprises a perimeter member 22 which has a circular shaped configuration. It is within the scope of the invention for the perimeter member 22 to have any configuration, including but not limited to circular-shaped, oval shaped, rectangular shaped, and square shaped. The perimeter member 22 can be engaged to the body of the stent 10 by at least one connector 44 as shown in FIG. 12.

A long member 24 is engaged to the perimeter member 22. In some embodiments one end of the long member 24 is directly engaged to the perimeter member 22, as shown in FIG. 10A-B. In other embodiments, the long member 24 is not directly engaged to the perimeter member 22, as shown for example in FIG. 11A. As shown in the FIGS. 10A and 10B, the long member 24 has a bend 30. However, it is within the scope of the invention for the long member 24 to be straight, curvilinear, or zig-zag. As used in this application a zig-zag member 42 or connector 44 has at least one bend along the length of the member 42/connector 44. As shown in FIG. 10A, the long member 24 has a first section 26 and a second section 28 engaged by the bend 30. Each section 26, 28 can have any length. Note that the number of bends 30 determines the number of sections that a long member 24 has. Thus, a long member 24 can have one, two three, four, five, six, seven, eight, nine or more sections.

The side branch 20 further comprises a first cell segment 32 and a second cell segment 34, which are engaged to the long member 24. As discussed above, the first and second cell segments 32, 34 define a bi-stable cell 48. In some embodiments, the segments 32, 34 are directly engaged to the long member 24 by a portion of the first cell segment 32, as shown, for example, in FIG. 10B. In other embodiments, the segments 32, 34 indirectly engaged to the long member 24 by at least one short member 42, as shown, for example, in FIG. 10C. The short member 42 can have any configuration, for example, but not limited to, straight, zig-zag, or curvilinear/curved.

Figure 10C:
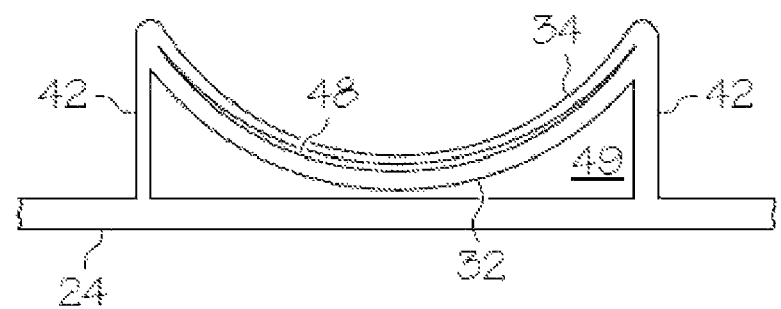
FIG. 10C is a view of the cell in FIG. 10B engaged to a portion of the side branch in an alternative manner.

As shown in FIG. 10C, the first cell segment 32 is engaged to the long member 24 by two short members 42. It is within the scope of the invention for the first cell segment 32 to be engaged to the long member 24 by any number of short members 42, for example, but not limited to one, two, three, four, five, six or more short members 42. As shown in FIGS. 10B, two short members 42, one at both ends of the segments 32, 34, engage the segments 32, 34 to the long member 24, in addition to the direct engagement of the first cell segment 32 to the long member 24. In this embodiment, the short member 42 should be engaged so as not to affect the ability of the second cell segment 34 to flip from the first state 36 to the second state 38. In some embodiment, the short members 24 are only engaged to any portion of the first cell segment 32.

In at least one embodiment, the second cell segment 34 is engaged to the adjacent long member 24. As shown in FIG. 10A, the second cell segment 34 is engaged to the bend 30 of the adjacent long member 24 by a connector 44. It is within the scope of the invention for the connector 44 to have any length and any configuration, for example, but not limited to straight, zig-zag, or curvilinear/curved. Although the connector 44 is shown being engaged to substantially the middle of the second cell segment 34, the connector 44 can be engaged anywhere along the length of the second cell segment 34.

The side branch 20 also has at least one petal 46. As shown in FIG. 10A, the side branch 20 has twelve petals 46. Thus, it is within the scope of the invention for the side branch 20 to have one, two, three, four, five, six, seven, eight, nine, ten, eleven, twelve, thirteen, fourteen, fifteen or more petals 46. As shown in FIG. 10A, each petal 46 engages two adjacent long members 24. In some embodiments, the petals 46 are engaged to the ends of the long members 24 and in other embodiments, the petals 46 are engaged to the end regions of the long members 24. As shown in FIGS. 16A-C, at least one portion of the petal 46 can form a cell segment 32, 34 of a bi-stable cell 48. The petal 46 in FIGS. 16A and 16B has one bi-stable cell 48 positioned approximately in the middle section of the petal 46.

It is within the scope of the invention for the petal 46 to have more than one bi-stable cell 48. For example, as shown in FIG. 16C, the petal 46 has two bi-stable cells 48 positioned opposite one another. Note that the first and second segments 32, 34 of the bi-stable cells 48 can have opposite configurations. For example, as shown in FIG. 16C, the first cell segment 32 of one cell 48 forms the proximal side of the bi-stable cell 48 while the first cell segment 32 of the second bi-stable cell 48 forms the distal side of the bi-stable cell 48. In some embodiments, not shown, a portion of the petal 46 forms a portion of a double bi-stable cell geometry.

FIG. 11A is a flat view of an example of another non-limiting configuration for a side branch 20 that has a plurality of bi-stable cells 48a and a plurality of cells 49 with one stable state. FIG. 11B is an enlarged view of a portion of the side branch 20 of FIG. 11A. As discussed above, the side branch 20 in FIG. 11A has bi-stable cells 48a, 48b that are two different sizes/have two different areas $A_1, A_2$. However, it is within the scope of the invention for the bi-stable cells 48a, 48b to be the same size/have the same area. Also, as discussed above, the first cell segment 32 of the bi-stable cell 48b can be directly engaged to the perimeter member 22 as shown in FIGS. 11A and 11B or the first cell segment 32 of the bi-stable cell 48b can be indirectly engaged to the perimeter member 22 in a manner similar to the indirect engagement of the bi-stable cell 48 to the long member 24 by the first cell segment 32, shown in FIG. 10C.

In the side branch 20 configuration of FIG. 11A, one end of the long member 24 is engaged to connector 44 instead of to the perimeter member 22, as shown in FIG. 10A. In FIG. 11A all the long members 24 are engaged to connectors 44, but it is within the scope of the invention for at least one of the long member 24 to be engaged to the perimeter member 22. In some embodiments, alternating long members 24 are engaged to the perimeter member 22 and alternating long member 24 are engaged to a connector 44. The connector 44 engages the long member 24 to the second cell segment 34 of bi-stable cell 48b. Although the connector 44 is engaged to substantially the middle of the second cell segment 34, as discussed above, the connector 44 can be engaged anywhere along the length of the second cell segment 34.

FIG. 12 is a perspective view of the side branch 20 of FIG. 11A and FIGS. 13-15 show the side branch 20 of FIG. 11A being expanded by a balloon which has been omitted in the figures. FIGS. 15A-C show different views, perspective view, side view and end view, respectively, of the expanded side branch 20 of FIG. 11A. In FIG. 12, the bi-stable cells 48 are in the first state 36. In FIGS. 13-14, the bi-stable cells 48 are transitioning to the second state 38. In FIG. 15A, the bi-stable cells 48 are in the second state 38.

FIG. 17 shows a non-limiting example of a side branch 20 configuration comprising a plurality of columns 50 of bi-stable cells 48. It is within the scope of the invention for the side branch 20 to have any number of columns 50 of bi-stable cells 48. In some embodiments, the side branch 20 has at least one column 50 that has both bi-stable cells 48 and cells 49 that are not bi-stable.

The bi-stable cells 48 in columns 50 have the same configuration in FIG. 17. However, in at least one embodiment, the bi-stable cells 48 in a column 50 have different configurations. In some embodiments, the side branch 20 comprises columns 50 which comprise bi-stable cells 48 having a plurality of configurations. In at least one embodiment, adjacent column 50 comprise bi-stable cells 48 having different configurations. Thus, for example, a first column 50 comprises bi-stable cells 48 having a first configuration and a second column 50 comprises bi-stable cells 48 having a second configuration, where the first and second configurations are different.

In some embodiments, the columns 50 are non-tapered. In other embodiments, the columns 50 are tapered, as shown, for example, in FIG. 17. In FIG. 17, the columns 50 are tapered because the bi-stable cells 48 closer to the perimeter member 22 are larger than the bi-stable cells 48 farther away from the perimeter member 22. In at least one embodiment, the side branch 20 comprises a plurality of columns 50 of bi-stable cells 48 where adjacent bi-stable cells 48 in a column 50 are offset from one another, as shown, for example, in FIG. 8E. In these side branch 20 embodiments, the size of the bi-stable cells 48 forming the columns 50 affects the amount of scaffolding provided by the side branch 20. Thus, a side branch 20 with fewer columns 50 with larger sized bi-stable cells 48 provide less scaffolding than a side branch 20 with more columns 50 with smaller sized bi-stable cells 48.

In at least one embodiment, the bi-stable cells 48 of the side branch 20 are arranged so that the side branch 20 extends farther into the side branch vessel when the side branch 20 is in an expanded state. For example, the bi-stable cells 48 are oriented so that the when the bi-stable cell 48 transitions to the second stable state 38, the second cell segment 34 assumes a position that is farther away from the tubular body of the stent. As shown in FIG. 17, adjacent columns 50 of bi-stable cells 48 are engaged by at least one connector 44. The connector 44 can have any length and any configuration, for example, but not limited to straight, zig-zag, curvilinear/curved. Note that if adjacent bi-stable cells 48, for example in a column 50, are engaged by a connector 44 that is configured to increase its longitudinal length upon the expansion of the side branch 20, for example a zig-zag connector 44, the side branch 20 will extend farther into the side branch vessel than if the connector 44 is configured to maintain its longitudinal length upon expansion. Thus, in some embodiments, the amount of vessel coverage by the side branch 20 is optimized by adjusting the orientation of the bi-stable cells 48 and the configuration(s) of the connectors 44 engaging adjacent bi-stable cells 48.

In at least one embodiment, the orientation of the bi-stable cells 48 affects the diameter of the side branch 20. In some embodiments, the side branch 20 comprises at least one ring 52 of bi-stable cells 48. In this embodiment, the bi-stable cells 48 extend about the circumference of the side branch 20. FIG. 18 is a non-limiting example of a side branch 20 with one ring 52 of bi-stable cells 48. The side branch 20 can have a plurality of rings 52 of bi-stable cells 48, with a first ring 52 engaged to the perimeter member 22, a second ring 52 engaged to the first ring 52, a third ring 52 engaged to the second ring 52 and so on. The rings 52 can be engaged to the perimeter member 22 and adjacent rings 52 by a plurality of connectors 44 which can have any length and configuration. Although each bi-stable cell 48 in the ring 52 is engaged to the perimeter member 22 in FIG. 18, it is within the scope of the invention for a portion of the bi-stable cells 48 in the ring 52 not to be engaged to the perimeter member, not shown. In this embodiment, the bi-stable cell 48 would only be engaged to adjacent bi-stable cells 48 in the ring 52.

In some embodiments, bi-stable cells 48 of adjacent rings 52 can be engaged either to a bi-stable cell 48b in the adjacent ring 52 by a connector 44c or to a connector 44a that is engaging adjacent bi-stable cells 48 in the adjacent ring 52, as shown, for example, in FIG. 18. In one embodiment, the connector 44a engaging adjacent bi-stable cells 48 in a ring 52 extends outward when the side branch 20 is expanded thereby extending the connector 44b engaged to the bi-stable cell 48a of the adjacent ring 52 further away from the perimeter member 22. This allows the rings 52 of bi-stable cells 48 to be nested when the side branch 20 is in the unexpanded state and separated from one another when the side branch 20 is in the expanded state so that the bi-stable cells 48 in the side branch 20 have enough space between one another to be in the second state 38. In other embodiments, adjacent rings 52 are engaged by connectors 44. Thus a bridging connector 44e engages a connector 44d in one ring 52 to a connector 44f in the adjacent ring 52, as shown, for example, in FIG. 18.

Adjacent bi-stable cells 48 within a ring 52 can be engaged by a connector 44. As discussed above, the connector 44 can have any configuration and length. In some embodiments, the connector 44 engaging adjacent bi-stable cells 48 in a ring 52 has a first configuration when the side branch 20 is in the unexpanded state and a second configuration when the side branch 20 is in the expanded state. Thus, if the adjacent bi-stable cells 48 are arranged so that the distance between the second segment 34 of one bi-stable cell 48 and the first segment 32 of the adjacent bi-stable cell 48 decreases upon expansion of the side branch 20, the first and second configurations of the connector 44 are different because the configuration of the connector 44 changes to accommodate the decreased distance between adjacent bi-stable cells 48.

Note that the diameter of the side branch 20 in this embodiment depends upon the number of bi-stable cells 48 in a ring 52 and the diameter of each bi-stable cell 48 in the second state 38. In some embodiments, each ring 52 has the same number of bi-stable cells 48. In some embodiments, the side branch 20 has rings 52 with different numbers of bi-stable cells 48. In one embodiment, the side branch 20 is tapered if the number of bi-stable cells 48 in the ring 52 engaged to the perimeter member 22 is greater than the end ring 52 of the side branch 20. In another embodiment, the side branch 20 is not tapered if the number of bi-stable cells 48 in the ring 52 engaged to the perimeter member 22 is less than the end ring 52 of the side branch 20. In some embodiments, the side branch 20 has at least one ring 52 that has bi-stable cells 48 and cells 49 that have only one stable state.

The following numbered statements characterize the embodiments described above:

1. A stent comprising a substantially cylindrical tubular body, the tubular body comprising at least one expandable side branch, the at least one side branch comprising:
   a first long member;
   a first cell segment, the first cell segment having a first width, the first cell segment engaged to a portion of the first long member; and
   a second cell segment, the second cell segment engaged to the first cell segment, the second cell segment having a second width, the second width being less than the first width of the first cell segment, the second cell segment having a first state and a second state, the first and second cell segments defining a first cell, the first cell having a first area when the second cell segment is in the first state, the first cell having a second area when the second cell segment is in the second state, the first area smaller than the second area.
2. The stent of statement 1, the first long member comprising a first section and a second section, the first section at an oblique angle to the second section, the first cell segment engaged to the first section of the first long member
3. The stent of statement 1, the first cell segment directly engaged to the first long member.
4. The stent of statement 3, further comprising at least one first short member, the first cell segment further engaged to the first long member by the at least one first short member.
5. The stent of statement 1, further comprising a first short member, the first cell segment indirectly engaged to the first long member by the first short member.
6. The stent of statement 1, the second cell segment having at least one hinge
7. The stent of statement 1, further comprising a perimeter member, the perimeter member defining a side branch opening, the first long member engaged to the perimeter member.
8. The stent of statement 1, the first cell segment having a first configuration in the first state, the second cell segment having a second configuration in the first state, the first and second configurations being the same.
9. The stent of statement 8, the first cell segment having the first configuration in the second state, the second cell segment having the second configuration in the second state.
10. The stent of statement 8, the first cell segment having the first configuration in the second state, the second cell segment having a third configuration in the second state, the third configuration different than the first configuration.
11. The stent of statement 1, the first cell segment having a first configuration in the first state, the second cell segment having a second configuration in the first state, the first and second configurations being the different.
12. The stent of statement 1, further comprising:
   a second long member;
   a first connector, the first connector having a first end and a second end, the first end engaged to the second cell segment and the second end engaged to the second long member.
13. The stent of statement 12, the second long member having a first bend, the second end of the first connector engaged to the first bend of the second long member.
14. The stent of statement 12, further comprising:
   a first petal, the first petal engaging the first member and the second member.
15. The stent of statement 14, the first long member having a first end, the second long member having a first end, the first petal engaging the first ends of the first and second long members.
16. The stent of statement 14, further comprising:
   a third cell segment, the third cell segment having a third width; and
   a fourth cell segment, the fourth cell segment engaged to the third cell segment, the fourth cell segment having a fourth width, the fourth width being less than the third width of the third cell segment, the fourth cell segment having a first state and a second state, the third and fourth cell segments defining a second cell, the second cell having a first area when the fourth cell segment is in the first state, the second cell having a second area when the second cell segment is in the second state, the first area smaller than the second area.
17. The stent of statement 16, the second area of the second cell being less than the second area of the first cell.
18. The stent of statement 16, the third cell segment being directly engaged to the perimeter member.
19. The stent of statement 16, further comprising at least one second short member, the third cell segment being engaged to the perimeter member by at least one second short member.
20. The stent of statement 16, the fourth cell segment being engaged to the first long member.
21. The stent of statement 20, further comprising:
   a second connector, the second connector engaging the fourth cell segment to the first long member.

The inventive stents may be made from any suitable biocompatible materials including one or more polymers, one or more metals or combinations of polymer(s) and metal(s). Examples of suitable materials include biodegradable materials that are also biocompatible. By biodegradable is meant that a material will undergo breakdown or decomposition into harmless compounds as part of a normal biological process. Suitable biodegradable materials include polylactic acid, polyglycolic acid (PGA), collagen or other connective proteins or natural materials, polycaprolactone, hylauric acid, adhesive proteins, co-polymers of these materials as well as composites and combinations thereof and combinations of other biodegradable polymers. Other polymers that may be used include polyester and polycarbonate copolymers. Examples of suitable metals include, but are not limited to, stainless steel, titanium, tantalum, platinum, tungsten, magnesium, gold and alloys of any of the above-mentioned metals. Examples of suitable alloys include platinum-iridium alloys, cobalt-chromium alloys including Elgiloy and Phynox, MP35N alloy, Platinum Enhanced Radiopaque Stainless Steel (PERSS), and nickel-titanium alloys, for example, Nitinol.

The inventive stents may be made of shape memory materials such as superelastic Nitinol or spring steel, or may be made of materials which are plastically deformable. In the case of shape memory materials, the stent may be provided with a memorized shape and then deformed to a reduced diameter shape. The stent may restore itself to its memorized shape upon being heated to a transition temperature and having any restraints removed therefrom.

The inventive stents may be created by methods including cutting or etching a design from a tubular stock, from a flat sheet which is cut or etched and which is subsequently rolled or from one or more interwoven wires or braids. Any other suitable technique which is known in the art or which is subsequently developed may also be used to manufacture the inventive stents disclosed herein.

In some embodiments the stent, the delivery system or other portion of the assembly may include one or more areas, bands, coatings, members, etc. that is (are) detectable by imaging modalities such as X-Ray, MRI, ultrasound, etc. In some embodiments at least a portion of the stent and/or adjacent assembly is at least partially radiopaque.

In some embodiments the at least a portion of the stent is configured to include one or more mechanisms for the delivery of a therapeutic agent. Often the agent will be in the form of a coating or other layer (or layers) of material placed on a surface region of the stent, which is adapted to be released at the site of the stent's implantation or areas adjacent thereto.

A therapeutic agent may be a drug or other pharmaceutical product such as non-genetic agents, genetic agents, cellular material, etc. Some examples of suitable non-genetic therapeutic agents include but are not limited to: anti-thrombogenic agents such as heparin, heparin derivatives, vascular cell growth promoters, growth factor inhibitors, Paclitaxel, etc. Where an agent includes a genetic therapeutic agent, such a genetic agent may include but is not limited to: DNA, RNA and their respective derivatives and/or components; hedgehog proteins, etc. Where a therapeutic agent includes cellular material, the cellular material may include but is not limited to: cells of human origin and/or non-human origin as well as their respective components and/or derivatives thereof. Where the therapeutic agent includes a polymer agent, the polymer agent may be a polystyrene-polyisobutylene-polystyrene triblock copolymer (SIBS), polyethylene oxide, silicone rubber and/or any other suitable substrate.

The above disclosure is intended to be illustrative and not exhaustive. This description will suggest many variations and alternatives to one of ordinary skill in this art. The various elements shown in the individual figures and described above may be combined or modified for combination as desired. All these alternatives and variations are intended to be included within the scope of the claims where the term "comprising" means "including, but not limited to".

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the invention. Those skilled in the art may recognize other equivalents to the specific embodiment described herein which equivalents are intended to be encompassed by the claims attached hereto.

The invention claimed is:

1. A stent comprising a substantially cylindrical tubular body, the tubular body having a first expandable side branch defining a side branch opening, the first side branch comprising:
   a plurality of members comprising
      a plurality of first cell segments, each first cell segment having a first width; and
      a plurality of second cell segments, each second cell segment having a second width, the first width greater than the second width;
   a plurality of first bi-stable cells positioned at regular intervals around the first side branch forming a first band of the first side branch, each first bi-stable cell entirely defined by one first cell segment and one second cell segment, each first bi-stable cell having a first stable state with a first stable cell geometry and a second stable state with a second stable cell geometry, wherein in the first stable state the first cell segment is parallel to the second cell segment;
   a plurality of second bi-stable cells positioned at regular intervals around the first side branch forming a second band of the first side branch, the second band adjacent to the first band, each second bi-stable cell entirely defined by one first cell segment and one second cell segment, each second bi-stable cell having a first stable state with a first stable cell geometry and a second stable state with a second stable cell geometry, wherein in the first stable state the first cell segment is parallel to the second cell segment;
   a plurality of long members, each long member having a first section, a second section, and a bend extending from the first section and the second section, a portion of the second section of each long member defining a portion of the side branch opening, each first bi-stable cell connected to the first section of a long member, and each second bi-stable cell connected to the first section of a long member.

2. The stent of claim 1, further comprising a second cell having only one stable cell geometry.

3. The stent of claim 2, the second cell defined in part by a portion of the second cell segment.

4. The stent of claim 3, the second cell further defined in part by at least one portion of the first cell segment 5. The stent of claim 1, the plurality of first cell segments comprising a primary first cell segment, the plurality of second cell segments comprising a primary second cell segment and a secondary second cell segment, the plurality of first bi-stable cells comprising
   a primary first bi-stable cell, the primary first bi-stable cell being entirely defined by the primary first cell segment and the primary second cell segment; and
   a secondary first bi-stable cell, the secondary first bi-stable cell being entirely defined by the primary first cell segment and the secondary second cell segment.

6. The stent of claim 5, the at least two different stable cell geometries of the primary first bi-stable cell comprising a first stable cell geometry and a second stable cell geometry, the at least two different stable cell geometries of the secondary first bi-stable cell comprising a third stable cell geometry and a fourth stable cell geometry, the first stable cell geometry and the third stable cell geometry being the same stable cell geometry.

7. The stent of claim 1, the at least two different stable cell geometries comprising a first stable cell geometry, an intermediate cell geometry and a second cell geometry, the first stable cell geometry being C-shaped, the intermediate cell geometry being irregular-shaped, the second cell geometry being polygonal.

8. The stent of claim 1, the second cell segment being in a different stable position in each of the at least two different stable cell geometries, the different stable position of the second cell segment in each of the at least two stable cell geometries being obtained when only a position of the second cell segment changes relative to a stable position of the first cell segment.

9. The stent of claim 1, wherein first stable cell geometry is a curvilinear configuration.

10. The stent of claim 1, the first side branch defining a side branch opening and further comprising a plurality of long members, each first bi-stable cell being engaged to a portion of a long member, a first end region of each long member defining a portion of the side branch opening.

11. The stent of claim 1, each first bi-stable cell having a first size, each second bi-stable cell having a second size less than the first size, each first bi-stable cell being connected to one second bi-stable cell and two other first bi-stable cells.

12. The stent of claim 1, the first side branch further comprising a plurality of petals, each petal connected to and extending between two long members, the plurality of petals forming a third band of the first side branch, the first band being between the second and third bands, the third band forming a distal end region of the first side branch and the second band forming a proximal end region of the first side branch.

13. The stent of claim 1, wherein each first bi-stable cell changes from one stable state to another stable state only when a force applied exceeds the equilibrium position, wherein an external force is required to maintain the first bi-stable cell in a position between the first and second stable states.

14. A stent comprising a substantially cylindrical tubular body, the tubular body having a first expandable side branch, the first side branch comprising:
   a plurality of members comprising
      a plurality of first cell segments, each first cell segment having a first width; and
      a plurality of second cell segments, each second cell segment having a second width, the first width greater than the second width;
   a plurality of first bi-stable cells positioned at regular intervals around the first side branch forming a first band of the first side branch, each first bi-stable cell entirely defined by one first cell segment and one second cell segment, each first bi-stable cell having a first stable state with a first stable cell geometry and a second stable state with a second stable cell geometry, wherein in the first stable state the first cell segment is parallel to the second cell segment;
   a plurality of second bi-stable cells positioned at regular intervals around the first side branch forming a second band of the first side branch, the second band adjacent to the first band, each second bi-stable cell entirely defined by one first cell segment and one second cell segment, each second bi-stable cell having a first stable state with a first stable cell geometry and a second stable state with a second stable cell geometry, wherein in the first stable state the first cell segment is parallel to the second cell segment;
   a plurality of petals, each petal connected to and extending between two long members, the plurality of petals forming a third band of the first side branch, the first band being between the second and third bands, the third band forming a distal end region of the first side branch and the second band forming a proximal end region of the first side branch.

15. The stent of claim 14, each first bi-stable cell having a first size, each second bi-stable cell having a second size less than the first size, each first bi-stable cell being connected to one second bi-stable cell and two other first bi-stable cells.

16. The stent of claim 14, wherein each first bi-stable cell changes from one stable state to another stable state only when a force applied exceeds the equilibrium position, wherein an external force is required to maintain the first bi-stable cell in a position between the first and second stable states.

* * * * *